US008821810B2

(12) United States Patent
Whitesides et al.

(10) Patent No.: US 8,821,810 B2
(45) Date of Patent: Sep. 2, 2014

(54) DEVICES AND METHODS FOR MULTIPLEXED ASSAYS

(75) Inventors: George M. Whitesides, Newton, MA (US); Katherine A. Mirica, Waltham, MA (US); Andres W. Martinez, Cambridge, MA (US); Chao-Min Cheng, Cambridge, MA (US); Scott T. Phillips, Cambridge, MA (US); Monica Mascareñas, Albuquerque, NM (US); Xinyu Liu, Cambridge, MA (US); Xiujun Li, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/576,804

(22) PCT Filed: Feb. 3, 2011

(86) PCT No.: PCT/US2011/023647

§ 371 (c)(1), (2), (4) Date: Oct. 23, 2012

(87) PCT Pub. No.: WO2011/097412

PCT Pub. Date: Aug. 11, 2011

(65) Prior Publication Data

US 2013/0034869 A1 Feb. 7, 2013

Related U.S. Application Data

(60) Provisional application No. 61/301,058, filed on Feb. 3, 2010.

(51) Int. Cl.
*G01N 33/52* (2006.01)
*B01L 3/00* (2006.01)

(52) U.S. Cl.
CPC ... *B01L 3/502738* (2013.01); *B01L 2300/0627* (2013.01); *B01L 2300/0887* (2013.01); *B01L 2300/126* (2013.01); *B01L 2200/10* (2013.01); *B01L 2300/0681* (2013.01); *B01L 2400/065* (2013.01); *B01L 2300/161* (2013.01)
USPC ........... 422/420; 436/518; 436/169; 436/530; 422/421; 422/425; 435/287.2; 435/288.5

(58) Field of Classification Search
CPC .... G01N 33/53; G01N 33/543; G01N 33/525
USPC .............. 422/50, 400–430, 500–507, 62–67; 435/286.1–286.4, 288.3–288.5; 436/43–54, 161–162, 170
See application file for complete search history.

(56) References Cited

U.S. PATENT DOCUMENTS 4,618,475 A 10/1986 Wang
4,668,564 A 5/1987 Orchard (Continued)

FOREIGN PATENT DOCUMENTS

CN 1553189 A 12/2004
CN 101533011 A 9/2009

(Continued)

OTHER PUBLICATIONS

Aikio, et al., "Bioactive Paper and Fibre Products: Patent and Literary Survey," VTT Working Papers 51, VTT-Work-51, 2006, 84 pages.

(Continued)

*Primary Examiner* — Melanie Y Brown
*Assistant Examiner* — Rebecca Martinez
(74) *Attorney, Agent, or Firm* — Wilmer Cutler Pickering Hale and Dorr LLP

(57) ABSTRACT

The disclosure provides low cost, portable three-dimensional devices for performing multiplexed assays. The devices comprise at least two substantially planar layers disposed in parallel planes, wherein one of the layers is movable relative to each other parallel to the planes to permit the establishment of fluid flow communication serially between the two layers.

34 Claims, 14 Drawing Sheets

(56) References Cited

U.S. PATENT DOCUMENTS

| | | | |
|---|---|---|---|
| 4,668,619 | A | 5/1987 | Greenquist et al. |
| 4,743,530 | A | 5/1988 | Farid et al. |
| 4,757,004 | A | 7/1988 | Houts et al. |
| 4,861,711 | A | 8/1989 | Friesen et al. |
| 5,120,544 | A | 6/1992 | Henley |
| 5,173,262 | A * | 12/1992 | Burtis et al. .................... 422/72 |
| 5,209,904 | A | 5/1993 | Forney et al. |
| 5,266,179 | A | 11/1993 | Nankai et al. |
| 5,279,944 | A | 1/1994 | Fabrizi et al. |
| 5,409,664 | A | 4/1995 | Allen |
| 5,648,252 | A | 7/1997 | Dumitriu et al. |
| 5,707,818 | A | 1/1998 | Chudzik et al. |
| 5,804,452 | A * | 9/1998 | Pronovost et al. ............ 436/514 |
| 5,834,226 | A | 11/1998 | Maupin |
| 5,858,392 | A | 1/1999 | Dumitriu et al. |
| 5,869,172 | A | 2/1999 | Caldwell |
| 5,897,522 | A | 4/1999 | Nitzan |
| 5,906,934 | A | 5/1999 | Grande et al. |
| 5,925,259 | A | 7/1999 | Biebuyck et al. |
| 5,941,862 | A | 8/1999 | Haynes et al. |
| 6,004,442 | A | 12/1999 | Choulga et al. |
| 6,025,203 | A | 2/2000 | Vetter et al. |
| 6,060,534 | A | 5/2000 | Ronan et al. |
| 6,180,239 | B1 | 1/2001 | Whitesides et al. |
| 6,202,471 | B1 | 3/2001 | Yadav et al. |
| 6,210,907 | B1 | 4/2001 | Cha |
| 6,284,072 | B1 | 9/2001 | Ryan et al. |
| 6,319,310 | B1 | 11/2001 | Wong et al. |
| 6,391,523 | B1 | 5/2002 | Hurditch et al. |
| 6,416,642 | B1 | 7/2002 | Alajoki et al. |
| 6,440,645 | B1 | 8/2002 | Yon-Hin et al. |
| 6,440,725 | B1 | 8/2002 | Pourahmadi et al. |
| 6,478,938 | B1 | 11/2002 | Paek et al. |
| 6,555,390 | B2 * | 4/2003 | Chandler ...................... 436/518 |
| 6,566,575 | B1 | 5/2003 | Stickels et al. |
| 6,642,408 | B2 | 11/2003 | Batlaw et al. |
| 6,761,962 | B2 | 7/2004 | Bentsen et al. |
| 6,783,735 | B2 | 8/2004 | Vanmaele et al. |
| 6,816,125 | B2 | 11/2004 | Kuhns et al. |
| 6,844,200 | B2 | 1/2005 | Brock |
| 6,877,892 | B2 | 4/2005 | Karp |
| 6,880,576 | B2 | 4/2005 | Karp et al. |
| 6,887,701 | B2 | 5/2005 | Anderson et al. |
| 6,919,046 | B2 | 7/2005 | O'Connor et al. |
| 6,931,523 | B1 | 8/2005 | Tomoson et al. |
| 6,935,772 | B2 | 8/2005 | Karp et al. |
| 6,951,682 | B1 | 10/2005 | Zebala |
| 6,951,757 | B2 | 10/2005 | Sabatini |
| 6,989,128 | B2 | 1/2006 | Alajoki et al. |
| 7,008,799 | B1 | 3/2006 | Zimmer et al. |
| 7,186,352 | B2 | 3/2007 | Morse et al. |
| 7,192,693 | B2 | 3/2007 | Bryant |
| 7,291,857 | B2 | 11/2007 | Tanaka et al. |
| 7,303,923 | B2 | 12/2007 | Hardman et al. |
| 8,206,992 | B2 | 6/2012 | Reches et al. |
| 2002/0187074 | A1 | 12/2002 | O'Connor et al. |
| 2002/0187560 | A1 | 12/2002 | Pezzuto et al. |
| 2003/0032203 | A1 | 2/2003 | Sabatini et al. |
| 2003/0148401 | A1 | 8/2003 | Agrawal et al. |
| 2004/0067166 | A1 | 4/2004 | Karinka et al. |
| 2004/0103808 | A1 | 6/2004 | Lochun et al. |
| 2004/0119070 | A1 | 6/2004 | Roach et al. |
| 2005/0136501 | A1 | 6/2005 | Kuriger |
| 2005/0145496 | A1 | 7/2005 | Goodsaid et al. |
| 2005/0169962 | A1 | 8/2005 | Bhatia et al. |
| 2005/0196702 | A1 | 9/2005 | Bryant et al. |
| 2005/0266582 | A1 | 12/2005 | Modlin et al. |
| 2006/0014003 | A1 | 1/2006 | Libera et al. |
| 2006/0038182 | A1 | 2/2006 | Rogers et al. |
| 2006/0088857 | A1 | 4/2006 | Attiya et al. |
| 2006/0130054 | A1 | 6/2006 | Bocking et al. |
| 2006/0226575 | A1 | 10/2006 | Maghribi et al. |
| 2007/0154355 | A1 * | 7/2007 | Berndt et al. ................. 422/100 |
| 2007/0179117 | A1 | 8/2007 | Reiner et al. |
| 2007/0196819 | A1 | 8/2007 | Asberg et al. |
| 2007/0224701 | A1 | 9/2007 | Rosenstein |
| 2007/0278097 | A1 | 12/2007 | Bhullar et al. |
| 2007/0298433 | A1 | 12/2007 | Sia et al. |
| 2009/0298191 | A1 | 12/2009 | Whitesides et al. |
| 2011/0111517 | A1 | 5/2011 | Siegel et al. |
| 2011/0123398 | A1 | 5/2011 | Carrilho et al. |
| 2011/0189786 | A1 | 8/2011 | Reches et al. |
| 2012/0181184 | A1 | 7/2012 | Whitesides et al. |
| 2012/0198684 | A1 | 8/2012 | Carrilho et al. |

FOREIGN PATENT DOCUMENTS

| | | | |
|---|---|---|---|
| EP | 2143491 | | 1/2010 |
| JP | 08233799 | A | 9/1996 |
| WO | WO-97/48257 | | 12/1997 |
| WO | WO-99/46644 | | 9/1999 |
| WO | WO-00/33078 | | 6/2000 |
| WO | WO-01/02093 | A2 | 1/2001 |
| WO | WO-01/25138 | | 4/2001 |
| WO | WO-03/015890 | A1 | 2/2003 |
| WO | WO-2004/006291 | A2 | 1/2004 |
| WO | WO-2004012862 | A2 | 2/2004 |
| WO | WO-2004/080138 | | 9/2004 |
| WO | WO-2005/090975 | | 9/2005 |
| WO | WO-2005/090983 | A2 | 9/2005 |
| WO | WO-2005/107938 | | 11/2005 |
| WO | WO-2005/109005 | A1 | 11/2005 |
| WO | WO-2006/018044 | | 2/2006 |
| WO | WO-2006/076703 | | 7/2006 |
| WO | WO-2007/029250 | | 3/2007 |
| WO | WO-2007/081848 | | 7/2007 |
| WO | WO-2007/116056 | | 10/2007 |
| WO | WO-2007145697 | A2 | 12/2007 |
| WO | WO-2008/049083 | | 4/2008 |
| WO | WO-2009/120963 | | 10/2009 |
| WO | WO-2009/121037 | A2 | 10/2009 |
| WO | WO-2009/121038 | | 10/2009 |
| WO | WO-2009/121041 | A2 | 10/2009 |
| WO | WO-2009/121043 | A2 | 10/2009 |
| WO | WO-2010/022324 | | 2/2010 |
| WO | WO-2010/102279 | A1 | 9/2010 |
| WO | WO-2010/102294 | A1 | 9/2010 |
| WO | WO-2011/097412 | | 8/2011 |

OTHER PUBLICATIONS

Author Unknown, "Focus: Lab on Paper, DOI: 10.1039/b814043j," Lab Chip, vol. 8, No. 12, Dec. 2008, pp. 1988-1991, XP002585318, The Royal Society of Chemistry.

Berggren, et al., "Paper Electronics and Electronic Paper," IEEE, Section 12: Flexible Systems, 2001, pp. 300-303.

Bracher, et al., "Heterogeneous Films of Ionotropic Hydrogels Fabricated from Delivery Templates of Patterned Paper," Adv. Mater., 2008, pp. 1807-1812.

Brooks, et al., "A Simple Artificial Urine for the Growth of Urinary Pathogens," Lett. Appl. Microbiol., 1997, 24, pp. 203-206.

Bruzewicz, et al., "Low-Cost Printing of Poly(dimethylsiloxane) Barriers to Define Microchannels in Paper," Anal. Chem., 2008, 80, pp. 3387-3392.

Bruzewicz, et al., "Paper: Fabrication of a Modular Tissue Construct in a Microfluidic Chip," Lab Chip, 2008, 8, pp. 663-671.

Campana, et al., "Double and Triple Staining Methods for Studying the Proliferative Activity of Human B and T Lymphoid Cells," Journal of Immunological Methods, 107, 1988, pp. 79-88.

Carrilho, et al., "Paper Microzone Plates," Analytical Chemistry, vol. 81, No. 15, Aug. 2009, pp. 5990-5998.

Carrilho, et al., "Understanding Wax Printing: A Simple Micropatterning Process for Paper-Based Microfluidics," Analytical Chemistry, vol. 81, No. 16 Aug. 2009, pp. 7091-7095.

Chadee, et al., "Increased Phosphorylation of Histone H1 in Mouse Fibroblasts Transformed with Oncogenes or Constitutively Active Mitogen-Activated Protein Kinase Kinase," The Journal of Biological Chemistry, vol. 270, No. 34, Aug. 1995, pp. 20098-20105.

Cheng, et al., "Clinical Analytics: Paper-Based ELISA," Agnew. Chem., 2010, 122, pp. 1-5.

(56) References Cited

OTHER PUBLICATIONS

Chin, et al., "Lab-on-a-chip Devices for Global Health: Past Studies and Future Opportunities," Lab Chip, 2007, 7, pp. 41-57, A Journal of The Royal Society of Chemistry.
Costerton, et al., "Bacterial Biofilms: a Common Cause of Persistent Infections," Science Mag., 1999, pp. 1318-1322.
Daar, et al., "Top Ten Biotechnologies for Improving Health in Developing Countries," Nature Genetics, vol. 32, Oct. 2002, pp. 229-232.
Derda, et al., "Paper-supported 3D Cell Culture for Tissue-Based Bioassays," PNAS, vol. 106, No. 44, Nov. 2009, pp. 18457-18462.
Donlan, "Biofilm Formation: A Clinically Relevant Microbiological Process," Healthcare Epidemiology, CID 2001:33, Oct. 2001, pp. 1387-1392.
Donlan, et al., "Biofilm Formation on Cast Iron Substrata in Water Distribution Systems," Wat. Res. vol. 28, No. 6, pp. 1497-1503, 1994.
Donlan, et al., "Reviews: Biofilms: Survival Mechanisms of Clinically Relevant Microorganisms," Clinical Microbiology Reviews, vol. 15, No. 2, Apr. 2002, pp. 167-193.
Dungchai, et al., "Electrochemical Detection for Paper-Based Microfluidics," Anal. Chem., 2009, 81, pp. 5821-5826.
Ebeling, "The Permanent Life of Connective Tissue Outside of the Organism," J. Exp. Med., 17, 1913, 15 pages.
Harrison, et al., "Methodology Article: High-Throughput Metal Susceptibility Testing of Microbial Biofilms," BMC Microbiology, 2005, 5:53, 11 pages.
International Search Report and Written Opinion of the International Searching Authority, the European Patent Office, for International Application No. PCT/US2007/081848, dated Jan. 28, 2009, 12 pages.
International Search Report and Written Opinion of the International Searching Authority, the European Patent Office, for PCT/US2010/026499, dated Jun. 16, 2010, 2 pages.
International Search Report and Written Opinion of the International Searching Authority, the Korean Intellectual Property Office, for International Application No. PCT/US2009/038566, dated Dec. 16, 2009, 10 pages.
International Search Report and Written Opinion of the International Searching Authority, the Korean Intellectual Property Office, for International Application No. PCT/US2009/038694 dated Nov. 12, 2009, 10 pages.
International Search Report and Written Opinion of the International Searching Authority, the Korean Intellectual Property Office, for PCT/US2009/038693, dated Oct. 28, 2009, 8 pages.
International Search Report and Written Opinion of the International Searching Authority, the Korean Intellectual Property Office, for PCT/US2009/038699, dated Oct. 28, 2009, 9 pages.
International Search Report and Written Opinion of the International Searching Authority, the Korean Intellectual Property Office, for PCT/US2009/038702, dated Nov. 11, 2009, 7 pages.
International Search Report of the International Searching Authority, the European Patent Office, for PCT/US2010/026547, dated Jul. 19, 2010, 3 pages.
International Search Report of the International Searching Authority, the Korean Intellectual Property Office, for PCT/US2009/054601, dated Mar. 22, 2010, 2 pages.
Klajn, et al., "Multicolour Micropatterning of Thin Films and Dry Gels," Nature Materials, vol. 3, Oct. 2004, pp. 729-735.
Lahav, et al., "DO1: 10.1002/adma.200601843—Patterning of Poly(acrylic acid) by Ionic Exchange Reactions in Microfluidic Channels," Advanced Materials, 2006, 18, pp. 3174-3178.
Leary, et al., "Rapid and Sensitive Colorimetric Method for Visualizing Biotin-Labeled DNA Probes Hybridized to DNA or RNA Immobilized on Nitrocellulose: Bio-Blots," PNAS, vol. 80, No. 13, 1983, pp. 4045-4049.
Li, et al., "Thread as a Versatile Material for Low-Cost Microfluidic Diagnostics," Applied Materials & Interfaces, vol. 2, No. 1, Jan. 2010, 6 pages.
Liu, et al., "Three-Dimensional Photopatterning of Hydrogels Containing Living Cells," Biomed. Microdevices, 2002, 4, pp. 257-266.
Lu, et al., "Short Communication: Rapid Prototyping of Paper-Based Microfluidics with Wax for Low-Cost, Portable Bioassay," Electrophoresis, 2009, 30, pp. 1497-1500.
Mabey, et al., "Diagnostics for the Developing World," Nature Reviews / Microbiology, vol. 2, Mar. 2004, pp. 231-240.
Martinez, et al., "Diagnostics for the Developing World: Microfluidic Paper-Based Analytical Devices," Analytical Chemistry, vol. 82, No. 1, Jan. 2010, pp. 3-10.
Martinez, et al., "FLASH: A Rapid Method for Prototyping Paper-Based Microfluidic Devices," Lab Chip, 2008, 8, pp. 2146-2150, A Journal of the Royal Society of Chemistry.
Martinez, et al., "Paper: Programmable Diagnostic Devices Made from Paper and Tape," Lab Chip, Jul. 2010, 6 pages.
Martinez, et al., "Patterned Paper as a Platform for Inexpensive, Low-Volume, Portable Bioassays," Agnew. Chem. Int. Ed., 2007, 46, pp. 1318-1320.
Martinez, et al., "Simple Telemedicine for Developing Regions: Camera Phones and Paper-Based Microfluidic Devices for Real-Time, Off-Site Diagnosis," Analytical Chemistry, vol. 80, No. 10, May 2008, pp. 3699-3707.
Martinez, et al., "Three-Dimensional Microfluidic Devices Fabricated in Layered Paper and Tape," PNAS, vol. 105, No. 50, Dec. 2008, pp. 19606-19611.
Matsumoto, et al., "Three-Dimensional Cell and Tissue Patterning in a Strained Fibrin Gel System," PLoS One, Nov. 2007, Issue No. 11, 6 pages.
Muller et al., "Automatic Paper Chromatography," Analytical Chemistry, vol. 21, No. 9, Sep. 1949, pp. 1123-1125.
Nelson, et al., "Three-Dimensional Lithographically Defined Organotypic Tissue Arrays for Quantitative Analysis of Morphogenesis and Neoplastic Progression," Nature Protocols, vol. 3, No. 4, 2008, pp. 674-678.
Nie et al., "Paper: Integration of Paper-based Microfluidic Devices with Commercial Electrochemical Readers," Lab Chip, Oct. 2010, 7 pages.
Peele, et al., "Semi-Automated vs. Visual Reading of Urinalysis Dipsticks," Clin. Chem, 1977, 23, pp. 2242-2246.
Pugia, et al., "High-Sensitivity Dye Binding Assay for Albumin in Urine," J. Clin. Lab. Anal. 1999, 13, pp. 180-187.
Reches, et al., "Thread as a Matrix for Biomedical Assays," Applied Materials & Interfaces, vol. xxx, No. xx, 000, xxxx, pp. A-G, 2010.
Shaw, et al., "Negative Photoresists for Optical Lithography," IBM Journal of Research and Development, vol. 41, No. 1/2, Jan./Mar. 1997, pp. 81-94, 15 pages.
Shimizu, et al., "Biofilm Formation on Hydrophilic Intraocular Lens Material," Current Eye Research, 31, 2006, pp. 989-997.
Sia, et al., "Microfluidic Devices Fabricated in Poly(dimethylsiloxane) for Biological Studies," Electrophoresis, 2003, 24, pp. 3563-3576.
Siegel, et al., "Foldable Printed Circuit Boards on Paper Substrates," Advanced Functional Materials, 2010, 20, pp. 28-35.
Smith, S.K., "Angiogenesis, Vascular Endothelial Growth Factor and the Endometrium," Hum. Reprod. Update 1998, 4, pp. 509-519.
Supplementary European Search Report and Written Opinion for European Application No. 09724164 dated Mar. 16, 2011, 7 pages.
Tang, et al., "Molding of Three-Dimensional Microstructures of Geis," J. Am. Chem. Soc., 2003, 125, pp. 12988-12989.
Urbich, et al., "Endothelial Progenitor Cells: Characterization and Role in Vascular Biology," Circulation Research, DOI: 10.1161/01.RES.0000137877.89448.78, Aug. 2004, pp. 343-353.
von Lode, P., "Point-of-care Immunotesting: Approaching the Analytical Performance of Central Laboratory Methods," Clinical Biochemistry, 38, 2005, pp. 591-606.

(56) References Cited

OTHER PUBLICATIONS

Washburn, E. W., "The Dynamics of Capillary Flow," The Physical Review, vol. XVII, No. 3, Second Series, Mar. 1921, pp. 273-283.
Winkleman, et al., "Patterning micron-sized features in a cross-linked poly (acrylic acid) film by a wet etching process," The Royal Society of Chemistry, 2007, pp. 108-116.
Xerox Corporation, "Material Safety Data Sheet for Xerox Phaser 6250 Color Laser Toner," 2003, pp. E-1-E-5, retrieved from http://www.office.xerox.com/userdoc/P6250/6250_Web/pdfs/msds.pdf.
Zhi, et al., "Multianalyte Immunoassay with Self-Assembled Addressable Microparticle Array on a Chip," Analytical Biochemistry, vol. 318, No. 2, Jul. 2003, pp. 236-243.
Zhu, et al., "Research Article: Proposal to Create Subspecies of *Rickettsia conorii* Based on Multi-Locus Sequence Typing and an Emended Description of *Rickettsia conorii*," BMC Microbiology, 2005, 5:11, 11 pages.
Office Action for Chinese Patent Application No. 201180014901.0 mailed Mar. 11, 2014. 23 pages.

* cited by examiner

DEVICES AND METHODS FOR MULTIPLEXED ASSAYS

CROSS-REFERENCE TO RELATED APPLICATIONS

This application is a national stage of International (PCT) Patent Application Serial No. PCT/US2011/023647, filed Feb. 3, 2011, and published under PCT Article 21(2) in English, which claims the benefit of and priority to U.S. Provisional Application Ser. No. 61/301,058, filed Feb. 3, 2010, the entire disclosure of the aforementioned U.S. provisional application is incorporated herein by reference.

GOVERNMENT SUPPORT CLAUSE

This invention was made with government support under grant HR0011-06-1-0050 awarded by DARPA. The government has certain rights in the invention.

FIELD OF INVENTION

The field of the invention is low-cost, easy to use diagnostic devices.

BACKGROUND

Simple, low-cost diagnostic technologies are an important component of strategies for improving health-care and access to health-care in developing nations and resource-limited settings. According to the World Health Organization, diagnostic devices for use in developing countries should be ASSURED (affordable, sensitive, specific, user-friendly, rapid and robust, equipment-free, and deliverable to end-users). Conventional ELISA is one of the most commonly used methods for detecting disease markers; however, current ELISA devices do not meet the requirements of an ASSURED diagnostic assay. Thus, there remains a need for multiplexed assay devices that are inexpensive, portable, and easy to construct and use.

SUMMARY OF THE INVENTION

The invention provides inexpensive, easy to use devices for quantitative or qualitative analysis of a fluid sample, typically an aqueous fluid sample such as a sample from the body, (e.g., blood, sputum, or urine), or an industrial fluid, or a water sample. The disclosed devices are particularly well adapted to conduct immunoassays, such as sandwich or competitive immunoassays, although they readily may be adapted to accommodate and execute many known assay formats by suitable design as disclosed herein. Thus, they may execute assay formats involving, for example, filtration, multiple incubations with different reagents or combinations of reagents, serial or timed addition of reagents, various incubation times, washing steps, etc. The devices are particularly effective for executing colorimetric assays, e.g., immunoassays with a color change as a readout, and are easily adapted to execute multiple assays simultaneously. They are extremely sensitive, simple to manufacture, inexpensive, and versatile.

In one aspect, the invention provides a family of two dimensional or three dimensional devices, for assay of a fluid sample (e.g., an aqueous fluid sample). The two dimensions are the length and width of sheet-like layers, and the third, or Z dimension, is the depth composed of the thickness of the multiple layers. In some embodiments the devices are two dimensional, meaning that they comprise a pair of single layers in the same plane. The devices all comprise at least first and second substantially planar members or layers disposed in the same or in parallel planes. Optionally, the members may be separated by a fluid impermeable coating or a separate layer or section disposed between adjacent members or stacked layers containing hydrophilic regions or reagent depots and defining one or more openings permitting fluid flow between layers. One of the members comprises plural hydrophilic regions defined by fluid-impermeable barriers defining boundaries. The other member defines a test zone for presentation of a sample for assay through which fluid can flow in a direction normal to the plane of the layer.

The first and second members are designed, by any mechanical means known, to be moveable relative to each other in a direction parallel to the plane(s) of the layers to permit establishment of fluid flow communication serially between respective hydrophilic regions and the test zone. At least one reagent is disposed in the device within one of the hydrophilic regions or in a separate layer or section in a layer in flow communication with one of the hydrophilic regions and also in flow communication with a test zone when the one hydrophilic region and test zone are in fluid flow communication, for example, when movement of said members relative to each other serves to register a test zone and a hydrophilic region.

In preferred and alternative embodiments the devices comprise at least two separate test zones so as to permit conducting multiple assays simultaneously, and optionally at least two reagents disposed in the device within or in flow communication with separate hydrophilic regions which become in flow communication with respective separate test zones when the respective layers are moved and the hydrophilic regions and test zones are in registration.

The devices may further comprise in the member including but separated from the test zone a positive and/or a negative control zone, or may comprise a plurality of positive control zones comprising known concentrations of an analyte. This is one way to enable assessment of concentration of an analyte in a sample when the result in a test zone is compared with the result in control zones of, for example, low, medium, and high concentration. Often, the device comprises plural reagents for treating a single sample, disposed in the device within or in flow communication with one or more of the hydrophilic regions and in flow communication with a test zone when the hydrophilic region and test zone are in fluid flow communication. Preferably, the reagent(s) function to develop color in a test zone (including gradations from white to black) as an indication of the presence, absence or concentration of an analyte in a sample.

The devices also may comprise a washing reagent, or plural wash reagents such as buffers or surfactant solutions, within or in fluid communication with a second hydrophilic zone, which washing reagent(s) function to wash an analyte bound to a test zone by removing unbound species therein when said second hydrophilic region and test zone are in fluid flow communication. In this respect, the device may additionally include a carrier fluid inlet, e.g., an inlet for application of water or buffer, and may define a series of adsorptive flow paths between the inlet and the hydrophilic regions. Also, the devices may include an adsorbent layer for drawing fluid from or through a hydrophilic region and through a test zone. Any reagent needed in the assay may be provided within, or in a separate adsorbent layer in fluid communication with a hydrophilic region. For example, without limitation, a blocking agent, enzyme substrate, specific binding reagent such as an antibody or sFv reagent, labeled binding agent, e.g., labeled antibody, may be disposed in the device within or in flow communication with one or more of the hydrophilic regions. The binding agent, e.g., antibody, may be labeled with an enzyme or a colored particle to permit colorimetric assessment of analyte presence or concentration. Where an enzyme is involved as a label, e.g., alkaline phosphatase (ALP) or horseradish peroxidase (HRP), an enzyme substrate may be disposed in the device within or in flow communication with one of the hydrophilic regions. Exemplary substrates for ALP include 5-bromo-4-chloro-3-indolyl phosphate and nitro blue tetrazolium (BCIP/NBT), and exemplary substrates for HRP include 3,3',5,5'-Tetramethylbenzidine (TMB), 3,3'-Diaminobenzidine (DAB), and 2,2'-azino-bis(3-ethylbenzthiazoline-6-sulphonic acid) (ABTS).

As noted above, the device preferably is designed to establish fluid flow communication between a hydrophilic region and a test zone by movement of the layers relative to each other to register vertically (in 3D structures) or horizontally (in 2D structures) the test zone and a hydrophilic region.

The test zone itself typically is an absorbent region of the layer which permits flow through the layer, and may comprise an immobilized analyte binder. The devices also may include a sample inlet in fluid communication with the test zone, which optionally may be fitted with a sample filter upstream of the test zone for removing particulates from the sample, e.g., red blood cells. A reagent reservoir also may be disposed upstream of and in fluid communication with a test zone to hold a releasable reagent for pre-treating a sample.

The devices may further comprise visual indicia of the establishment of fluid communication of a test zone with plural said hydrophilic regions, for example, the indicia may comprise markings on one layer which register with an edge or a corresponding mark on the other layer when a test zone and hydrophilic region are registered in flow communication.

The devices may be adapted to detect the presence or concentration of essentially any analyte whose detection involves one or a series of incubation steps, or admixing with one or more reagents, to produce a signal detectable by machine or visually. Non limiting examples of analytes include viral antigens, bacterial antigens, fungal antigens, parasitic antigens, cancer antigens, and metabolic markers.

The layers of the devices preferably comprise a material selected from the group consisting of paper, cloth, or polymer film such as nitrocellulose or cellulose acetate. The fluid-impermeable barriers that define boundaries of the hydrophilic regions may be produced in adsorbent sheet material by screening, stamping, printing or photolithography and may comprise a photoresist, a wax, or a polymer that is impermeable to water when cured or solidified such as polystyrene, poly(methylmethacrylate), an acrylate polymer, polyethylene, polyvinylchloride, a fluoropolymer, or a photo-polymerizable polymer that forms a hydrophobic polymer.

In an exemplary embodiment, the three-dimensional devices are three-dimensional microfluidic paper-based analytical devices (3D-μPAD) for performing multiplexed assays (e.g., multiple ELISAs).

In another aspect, the invention provides assay methods comprising providing the device as described above, adding a sample to the test zone, and moving one layer in relation to another to establish serially fluid communication between the test zone and the hydrophilic zones. This permits fluid flow between respective hydrophilic regions and the test zone for a time interval and "automatic" execution of multiple steps of the assay. Examination of the test zone permits determination of the presence, absence, or concentration of an analyte. Preferably, the assay protocol produces a color reaction, which may include the development of a grey scale from black to white, and the examination of the development of, or intensity of, the color in the test zone to determine the presence, absence, or concentration of said analyte. The method may include an additional step of creating digital data indicative of an image of a developed test zone, e.g., taking a digital photograph of the test zone, and therefore of the assay result, and transmitting the data remotely for analysis to obtain actionable diagnostic information.

In one aspect, the invention provides a family of two-dimensional assay devices. The devices comprise at least a first and a second substantially planar layer disposed in parallel in the same Z plane. The layers may be fabricated from hydrophobic material, or hydrophilic material treated using methods known to create fluid impervious barriers on the material. One or more hydrophilic regions in both layers may be defined by fluid impervious boundaries.

DETAILED DESCRIPTION OF THE INVENTION

Portable, two and three-dimensional microfluidic analytical devices are described for performing multiplexed assays. The disclosed devices require the addition of one or more drops of sample (e.g., 2-10 μL) and one or a more drops of water (e.g., 40 μL) to perform the multiplexed assays. In preferred embodiments, all the reagents, buffer salts, analytes (e.g., antigens), and binders (e.g., antibodies) used for the assays may be stored within the device. The results of the multiple assays can be quantitative or qualitative and may be transmitted from the point of use to a remote location, e.g., for interpretation, using an imaging device, such as a camera phone or a portable scanner.

The devices disclosed herein will first be described in their broadest overall aspects with a more detailed description following.

Figure 1:
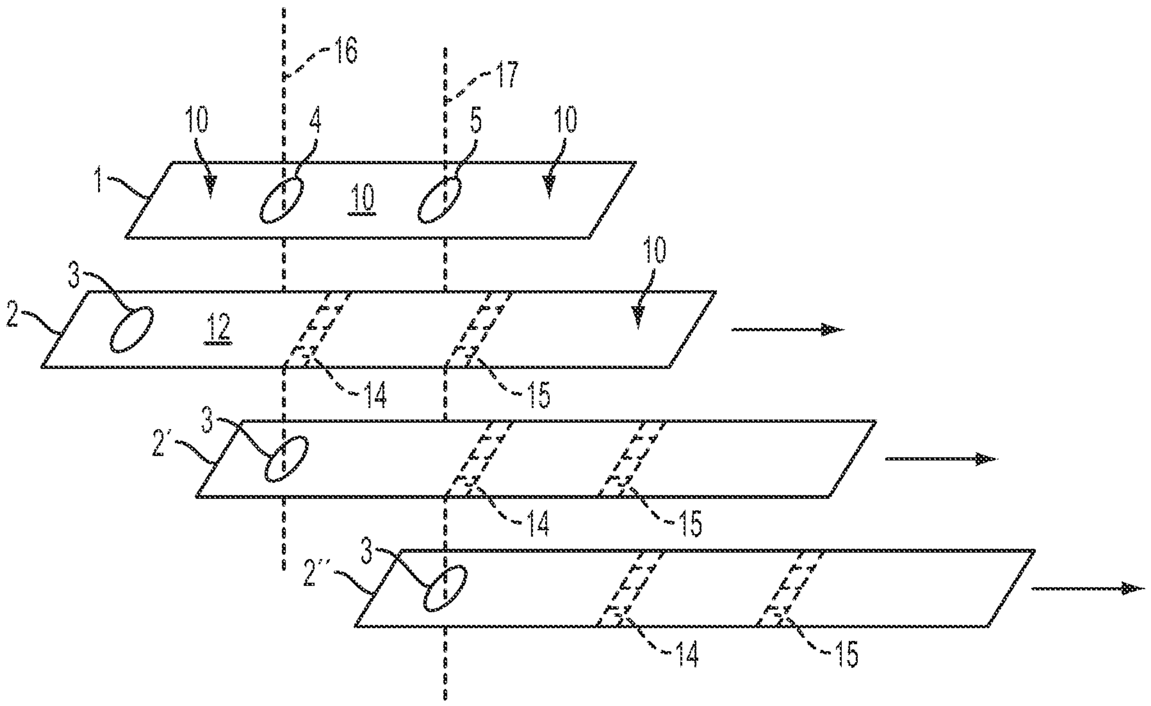
FIG. 1 is a schematic, exploded, perspective view of a portion of a device constructed in accordance with the invention illustrating certain principles underlying the structure and operation of the devices.

FIG. 1 depicts a pair of layers 1 and 2 fabricated from material having designed fluid impermeable or hydrophobic regions and hydrophilic, water adsorbent regions. They can be made, for example, from hydrophilic material treated using methods known to create water impervious barriers on the material, and as here illustrated may be disposed in planes parallel to one another. Layers 1 and 2 in practice preferably are in face-to-face contact, or are separated by a thin, fluid impervious interlayer with perforations defining openings permitting fluid flow therethrough (not shown), but in any case are adapted for relative movement, e.g., sliding. The layers slide in a direction parallel to the plane of the layers. Barrier sections 10 of layer 1 and 12 of layer 2 define boundaries of hydrophilic regions 3, 4, and 5. The barrier sections penetrate layers 1 and 2 and operate to channel fluid flow in a direction normal to the planes of the layers (also may be referred to as strips). Hydrophilic region 3 defines a test zone for application of a fluid sample held initially therein by adsorption. The test zone may comprise, for example, an immobilized binder for the analyte of interest. Region 4 in this exemplary embodiment serves as a fluid flow path to wash components of the sample during the assay; and region 5 holds a mobile assay development reagent, such as a mobile, colored particle-labeled, fluorophore labeled, or enzyme labeled binder, e.g., an antibody. Optionally, a third layer, comprising a hydrophilic, fluid-adsorptive reservoir (not shown), is disposed below layer 2 as a means of drawing fluid through the hydrophilic regions. Also optionally, the device may include, above layer 1, one or more layers defining flow paths, fluid inlets, filters or the like designed as disclosed herein to deliver fluid to the hydrophilic regions in the layers.

In operation, a sample suspected to contain an analyte is applied to test zone 3 and a fluid, typically an aqueous fluid such as a buffer, is applied to regions 4 and/or 5. Thereafter, layer 2 is moved laterally, e.g., as the user grasps the right end of layer 2 and pulls, until mark 15 on layer 2 is exposed beyond the edge of layer 1. In this position, illustrated as layer 2', region 4 and test zone 3 are in vertical registration, and fluid flows through and from region 4, and through the test zone 3, along axis 16, washing to remove from the test zone 3 unbound components of the sample disposed therein. After a time interval, layer 2 is moved further, until mark 14 is exposed, illustrated as layer 2". In this position, fluid containing development reagents disposed in region 5 pass along axis 17, interact with the sample, and develop a color, or other signal indicative of the presence, absence, or concentration of analyte in the sample. Layer 2 then may be moved further, e.g., out of contact with layer 1, and the test zone may be read with the naked eye or by appropriate machine (e.g., a portable scanner) or imaged with a camera phone or other device for transmission and analysis of the image.

Figure 2:
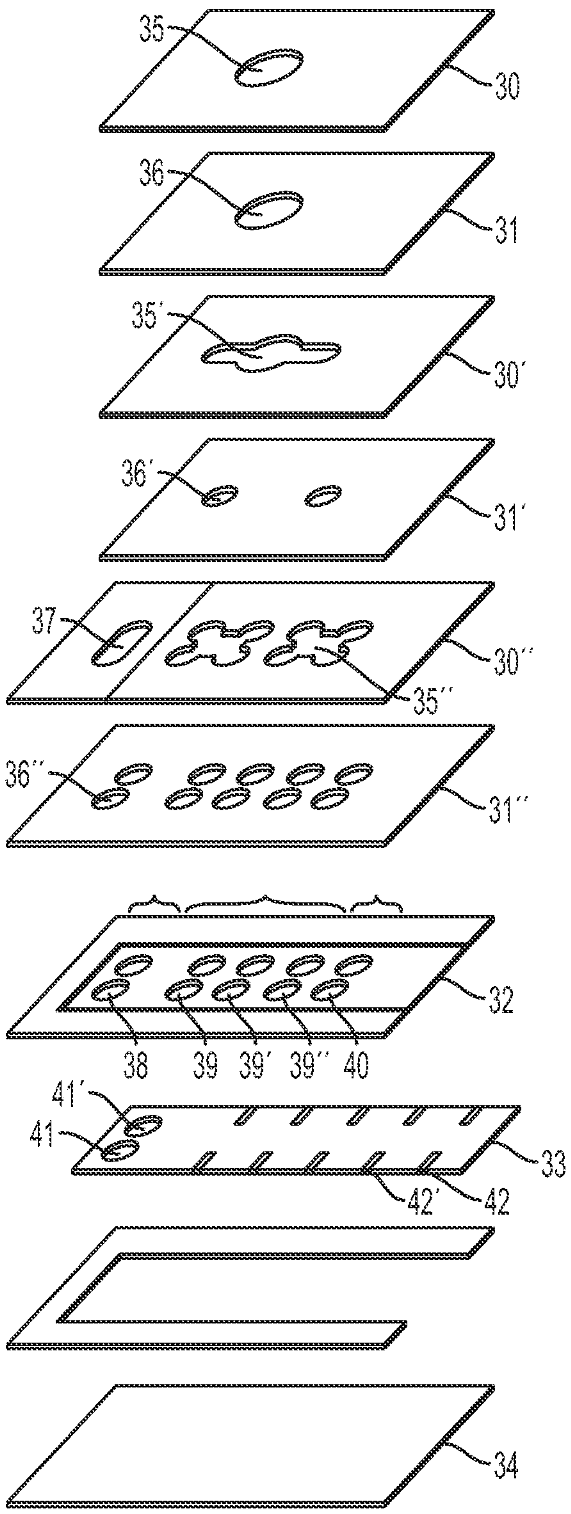
FIG. 2 is a schematic, exploded perspective view of a portion of a device showing multiple stacked substantially planar layers disposed in parallel planes comprising intervening fluid impervious layers, reagent disposed in one of the stacked layers, and a movable layer with two test zones.
Figure 3A:
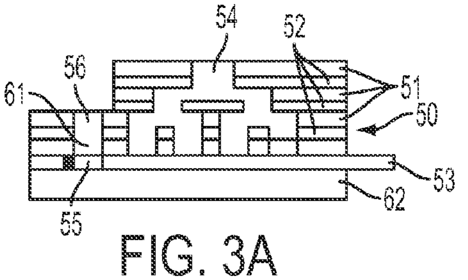
FIG. 3 (A-G) is a schematic diagram showing an assembled device in cross-section comprising a stationary piece with a carrier fluid inlet and sample inlet and a moveable layer comprising a test zone.
Figure 3B:
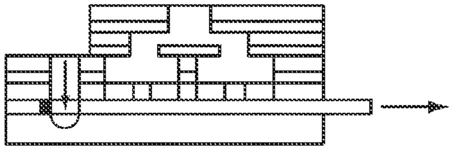
Figure 3C:
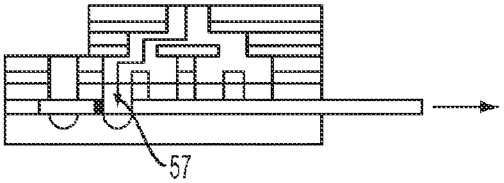
Figure 3D:
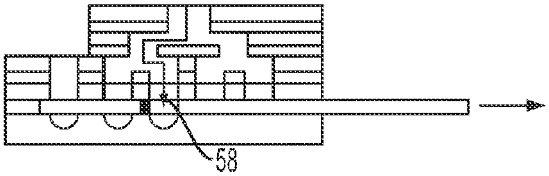
Figure 3E:
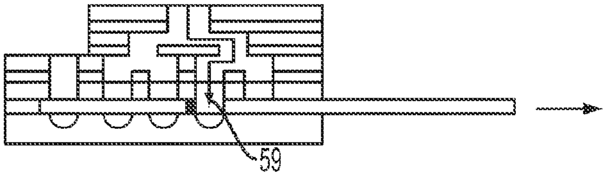
Figure 3F:
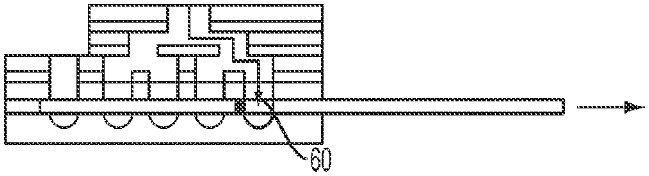
Figure 3G:
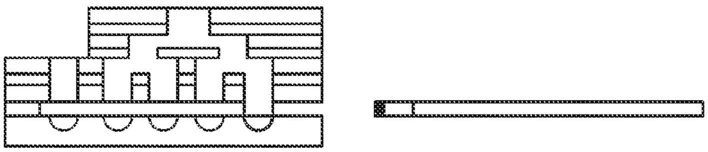

FIG. 2 provides another embodiment of the devices disclosed herein. FIG. 2 depicts a multilayer three-dimensional device. Layers 30, 30' and 30" are fabricated from hydrophobic material, or hydrophilic material treated using methods known to create water impervious barriers on the material, disposed as substantially planar layers in planes parallel to one another. The water impervious barriers on layer 30 define boundaries of a hydrophilic region 35 for establishing fluid flow communication between layers. Layers 30' and 30" comprise hydrophilic regions 35' and 35" that are in fluid flow communication with hydrophilic region 35. In this exemplary embodiment, fluid impermeable barriers 31, 31', and 31" (e.g., interlayers) are disposed between the layers of hydrophilic material 30, 30', 30" and 32. The fluid impermeable interlayers 31 comprise one or more perforations in the layer to define openings 36 for fluid flow communication between hydrophilic regions 35 and 35'. The openings 36 and 36' in the fluid impermeable interlayers can form channels within the stacked multilayer device providing fluid flow communication between hydrophilic regions. Layer 32 is a layer of hydrophilic material treated using known methods to create water impervious barriers defining a plurality of hydrophilic regions 38, 39, 39', 39" and 40. The hydrophilic regions disposed in layer 32 may comprise various reagents (e.g., reagents for blocking, binding antigen, or detecting the presence of an analyte). Alternatively, the hydrophilic regions disposed in layer 32 may be used for washing, in which case the region may not comprise any reagents (e.g., reagents for blocking, binding antigen, or detecting the presence of an analyte). Layer 33 is a layer of hydrophilic material treated using known methods to create water impervious barrier zones defining hydrophilic regions or test zones 41, 41' for assaying a sample. Layer 33 is adapted for relative movement within the device, e.g., lateral movement, e.g., sliding. Layer 33 slides in a direction parallel to the plane of the multilayer three-dimensional device, and here from left to right.

Hydrophilic region 37 in this exemplary embodiment serves as an inlet for sample addition, and is in fluid flow communication with test zones 41 and 41'. An additional (optional) planar layer 34 comprising a hydrophilic adsorptive reservoir is disposed at the base of the device. The hydrophilic adsorptive reservoir functions to provide a source of wicking to draw fluid through the hydrophilic regions. Optionally, the device may include one or more fluid inlets, filters or the like designed as disclosed herein to deliver fluid to the hydrophilic regions in the device.

In operation, a sample suspected to contain an analyte is applied to hydrophilic region 37 which is in fluid flow communication with test zones 41 and 41'. Analyte may be bound in the test zones 41 41' by an immobilized binder disposed therein. A fluid, typically an aqueous fluid such as a buffer or water, is applied to hydrophilic region 35. Thereafter, layer 33 is moved laterally, e.g., as the user grasps the right end of layer 33 and pulls until mark 42 on layer 33 is exposed beyond the end of the stacked layers. In this position, test zones 41 and 41' are aligned in registration with hydrophilic region 38 comprising a first reagent (e.g., an enzyme-labeled antibody). Fluid, e.g., water or buffer, is added to hydrophobic region 35 providing fluid flow from hydrophilic region 35 through the defined channels through to the test zones 41 and 41'. Fluid flow communication between hydrophobic region 38 and the test zones 41 and 41' results in addition of the first reagent to the test zones. After a time interval, layer 33 is further moved laterally until a second mark 42' on layer 33 is exposed beyond the end of the stacked layers. In this position, test zones 41 and 41' are aligned in registration with hydrophilic region 39. In this exemplary embodiment, hydrophilic region 39 does not comprise a reagent, but is used for washing unbound first reagent from the test zones. Washing solution, e.g., water or buffer, e.g., PBS, may be added to region 35, which passes from region 35 through the hydrophilic regions in fluid flow communication with the test zones. As shown in this exemplary embodiment, layer 33 may be moved laterally through the device to position the test zones 41 and 41' in register with hydrophilic region 39' and then moved to hydrophilic region 39" for an additional washing steps. At each position, after a time interval, washing solution, e.g., water or buffer, e.g., PBS may be added to region 35 to wash the test zones. Alternatively, the solutes of a buffer may be disposed in dry form within the device and water first entrains dissolves the solutes and the thus constituted buffer washes the test zone. After a time interval, layer 33 is further moved laterally until the last alignment mark on layer 33 is exposed beyond the end of the stacked layers. In this position, fluid containing development reagents disposed in hydrophilic region 40 move from the reagent layer 32 into the test zones 41 and 41'. The development reagents interact with the sample and develop a color, or other signal indicative of the presence, absence or concentration of analyte in the sample. Layer 33 may be moved further, e.g., out of contact with stacked multilayer device, and the test zones may be read with the naked eye or by an appropriate machine, e.g., a portable scanner. Alternatively, a picture of the test zones may be taken by camera phone and transmitted electronically for further analysis.

FIG. 3 shows a cross-section of the exemplary multilayered device 50 depicted in FIG. 2. FIG. 3 depicts the channels between the layers of hydrophilic material 51 and fluid impermeable interlayers 52. Layer 53 is adapted for lateral movement within the device. Layer 62 comprises a hydrophilic absorptive reservoir disposed at the base of the device. Layer 61 comprises a plurality of hydrophilic regions defined by fluid impervious barriers. The hydrophilic regions of layer 61 contain reagents for the assay disposed therein. As depicted in FIG. 3, the device 50 comprises layers defining a hydrophilic region 55 that defines a test zone for application of a fluid sample. As shown in this exemplary embodiment, test zone 55 may be in registration (i.e., alignment) with the sample inlet 56 (see FIG. 3*a*). Sample is loaded into the device by adding sample through the sample inlet 56 where it is disposed in the test zone 55 and, optionally, may be bound by an immobilized binder for the analyte in the test zone (see FIG. 3*b*). Layer 53 is moved laterally in the device to a first mark or stop on the layer, which is in register with a first reagent zone or in fluid communication with a first reagent zone (not shown). Buffer or water added to the multilayered three-dimensional device through inlet 54 provides fluid flow communication between to the first reagent zone and the test zone(s), and the reagent contained in the first reagent zone passes to the test zone 57 (see FIG. 3*c*). Layer 53 is further moved laterally in the device to a second mark or stop, which is in register with a second reagent zone (see FIG. 3*d*) or in fluid communication with a second reagent zone (not shown). The buffer or water is added to the device through region 54 to provide fluid flow communication between the second reagent layer and the test zone, and the reagent contained in second reagent zone passes through to the test zone. After a time interval, layer 53 can be moved to multiple positions as shown in FIG. 3*e-f* for exposure to multiple reagents or wash steps. After a further time interval, layer 53 is moved to a position placing it in register with detection reagents comprised in region 60 (see FIG. 3*f*) or placed in fluid flow communication with detection reagents comprised in region 60. In this position, water or buffer is added to region 54, which passes through the device and the development reagents disposed in region 60 pass from region 60 into the test zone, interact with the sample, and develop a color, or other signal indicative of the presence, absence, or concentration of the analyte in the sample. Layer 53 may be moved further, e.g., out of contact with the device 50, and the test zone maybe read with the naked eye or by an appropriate analytical device (e.g., a portable scanner), or a picture of the test zone may be taken by camera phone and transmitted electronically for further analysis.

How to Make The Assay Device

The devices described herein comprise at least two substantially sheet-like or planar layers members disposed in the same or in parallel planes. Each layer comprises one or more hydrophilic regions defined by fluid-impermeable barriers. The layers may be fabricated from porous, hydrophilic, adsorbent sheet materials, which include any hydrophilic substrates that wick fluids by capillary action. In one or more embodiments, the porous, hydrophilic layer is paper. Non-limiting examples of porous, hydrophilic layers include chromatographic paper, filter paper, cellulosic paper, filter paper, paper towels, toilet paper, tissue paper, notebook paper, Kim Wipes, VWR Light-Duty Tissue Wipers, Technicloth Wipers, newspaper, cloth, or polymer film such as nitrocellulose and cellulose acetate. In exemplary embodiments, porous, hydrophilic layers include chromatography paper, e.g., Whatman chromatography paper No. 1.

Hydrophilic materials may be patterned with fluid impermeable barriers to define boundaries of plural hydrophilic regions. Hydrophilic materials may be patterned using methods known the art, e.g., as described in U.S. Patent Publication No. US 2009/0298191, PCT Patent Publication No. WO2009/121037, and PCT Patent Publication No. WO2010/102294. Exemplary methods for patterning hydrophilic materials with fluid impermeable barriers include screening, stamping, printing, or photolithography.

In certain embodiments, the hydrophilic material is soaked in photoresist, and photolithography is used to pattern the photoresist to form fluid impervious barriers following the procedures described in, e.g., PCT Patent Publication No. WO2009/121037. Photoresist for patterning porous, hydrophilic material may include SU-8 photoresist, SC photoresist (Fuji Film), poly(methylmethacrylate), nearly all acrylates, polystyrene, polyethylene, polyvinylchloride, and any photopolymerizable monomer that forms a hydrophobic polymer.

Micro-contact printing may also be used to create fluid impervious barriers defining hydrophilic regions in the disclosed devices. For example, a "stamp" of defined pattern is "inked" with a polymer, and pressed onto and through the hydrophilic medium such that the polymer soaks through the medium; thus, forming barriers of that defined pattern.

In other embodiments, patterns of fluid impervious barriers are created on the hydrophilic layers by wax printing, such as by methods described in e.g., PCT Patent Publication No. WO2010/102294. For example, wax material may be hand-drawn, printed, or stamped onto a hydrophilic substrate. In embodiments where the wax material is a solid ink or a phase change ink, the ink can be disposed onto paper using a paper printer. Particular printers that can use solid inks or phase change inks are known in the art and are commercially available. One exemplary printer is a Phaser™ printer (Xerox Corporation). In such embodiments, the printer disposes the wax material onto paper by initially heating and melting the solid ink to print a preselected pattern onto the paper. The printed paper may be subsequently heated, e.g., by baking the paper in an oven, to melt the wax material (solid ink) to form hydrophobic barriers.

The wax material can be disposed onto a hydrophilic substrate in any predetermined pattern, and the feature sizes can be determined by the pattern and/or the thickness of the substrate. For example, a device can be produced by printing wax lines onto paper (e.g., chromatography paper) using a solid ink printer. The dimensions of the wax lines can be determined by the feature sizes of the device and/or the thickness of the paper. For example, the wax material can be printed onto paper at a line thickness of about 100 μm, about 200 μm, about 300 μm, about 400 μm, about 500 μm, about 600 μm, about 700 μm, about 800 μm, about 900 μm, about 1 mm, or thicker. The thickness of the wax to be printed can be determined by, e.g., analyzing the extent to which the wax permeates through the thickness of the substrate after heating. The wax material may be patterned on one or both sides of the hydrophilic material.

It is contemplated herein that the layers of a disclosed three-dimensional multilayered device may be fabricated using multiple methods for creating fluid impervious barriers. For example, the moveable layer comprising the test zone may be fabricated using one method to create certain properties useful for binding an antigen in the test zone, whereas the other hydrophilic layers may be fabricated using a different method for creating fluid impervious barriers. In certain embodiments, the moveable layer may be fabricated from hydrophilic material soaked in a photoresist and patterned by photolithography to create one or more test zones in the moveable test layer. Other layers of the device may be fabricated from hydrophilic material patterned using wax printing to define one or more hydrophilic regions for fluid flow communication between the parallel layers in face-to-face contact.

The devices described herein may optionally include one or more fluid impermeable layers disposed between the plural hydrophilic regions. These intervening impermeable barrier layers may comprise openings permitting fluid flow communication between hydrophilic regions. The fluid impermeable barriers may be comprise a film applied, for example, as a tape or as a coating or adhesive layer interposed between functional layers.

One or more optional fluid-impermeable layers are substantially planar and are arranged in parallel planes to one another. The fluid-impermeable layer is typically a planar sheet that is not soluble in the fluid of the microfluidic device and provides a desired level of device stability and flexibility. In certain embodiments, the fluid-impermeable layer is a plastic sheet, an adhesive sheet, or tape. In some embodiments, double-sided tape is used as the fluid-impermeable layer. Double-sided tape adheres to two adjacent layers of porous hydrophilic material (e.g., porous hydrophilic material treated using methods to produce fluid impervious barriers) and may be used to bind to other components of the microfluidic device. It is impermeable to water, and isolates fluid streams separated by less than 200 μm. In addition, it is also sufficiently thin to allow adjacent layers of paper to contact through holes punched in the tape (e.g., perforations) when compressed. It can easily separate from the paper to which it adheres and, thus, allows for disassembly of stacked devices and it is inexpensive and widely available.

Non-limiting examples of a fluid-impermeable layer includes Scotch® double-sided carpet tape, 3M Double Sided Tape, Tapeworks double sided tape, CR Laurence black double sided tape, 3M Scotch Foam Mounting double-sided tape, 3M Scotch double-sided tape (clear), QuickSeam splice tape, double sided seam tape, 3M exterior weather-resistant double-sided tape, CR Laurence CRL clear double-sided PVC tape, Pure Style Girlfriends Stay-Put Double Sided Fashion Tape, Duck Duck Double-sided Duct Tape, and Electriduct Double-Sided Tape. As an alternative to double-sided tape, a heat-activated adhesive can be used to seal the fluid-carrying layers together. Indeed, any fluid-impermeable material that can be shaped and adhered to the pattern hydrophilic layers can be used. In addition, it is also possible to use the same material that is used to pattern the paper layers to join the layers of paper together.

The intervening fluid impermeable layer(s) may be perforated with one or more openings to define channels that permit the establishment of fluid flow communication between the hydrophilic layers and/or the test zone(s).

The devices described herein comprise a substantially planar layer which defines at least one test zone for presentation of a sample in the assay device. In exemplary embodiments, the layer comprising one or more test zones is a moveable layer that moves (e.g., slides) within a parallel plane of the three-dimensional device. Alternatively, the member holding the test zone may be stationary and the other members adapted for movement. In some embodiments, a test layer may be a separate layer from the device, such that it can be inserted into the device, laterally pulled through the device (e.g., sliding), and/or removed from the device for analysis of one or more test zones. Alternatively, the device may be assembled with a test layer including a tab so that the test layer can be slid laterally through the device and/or removed from the device for analysis of one or more test zones. In an exemplary embodiment, the test layer may be pulled (e.g., pulled laterally through the assay device by an operator of the device; see, e.g., FIG. 1) to one or more predefined positions (or until a mark indicated on the test layer is exposed or placed in alignment with a corresponding mark on the stationary portion of the device) placing the test zone in fluid communication with one or more hydrophilic regions comprising one or more reagents. At each predefined position in the test layer, the test zone is placed in fluid flow communication with a reagent disposed in the reagent layer allowing the operator of the device to control and manipulate two or more steps of a multiple-step assay. In exemplary embodiments, as the test layer is slid through the device, the test zone(s) disposed in the test layer are exposed to two or more reagents for detecting the presence or absence of an analyte in a sample.

The test zone itself typically is an absorbent region of the layer which comprises it (e.g., porous, hydrophilic material). The test zone permits flow through the test layer. The test zone optionally may comprise an immobilized analyte binder (e.g., an antibody, a binding ligand, or a receptor). A test layer may be fabricated to include a plurality of test zones. For example, a test layer may include one or more test zones for determining the presence or absence of one or more analytes in the sample. The test layer may also include test zones that comprise positive or negative controls that are run in parallel to a sample test. In some embodiments, the test layer may include two or more positive control zones each comprising a different concentration of a known analyte to provide a method for quantifying the amount of analyte in the sample.

A fluid sample (e.g., an aqueous fluid sample) may be added directly to a test zone. Alternatively, a fluid sample (e.g., an aqueous fluid sample) may be added to a sample inlet that is fluid communication with one or more test zones. Optionally, the devices may be fitted with a sample filter upstream of and in fluid communication with the test zone for removing particulates from the sample, e.g., red blood cells. A reagent reservoir also may be disposed upstream of and in fluid communication with a test zone to hold a releasable reagent for pre-treating a sample.

Reagents and the Reagent Layer

The device comprises plural reagents disposed in hydrophilic regions defined by fluid impervious barriers. The hydrophilic regions comprising reagents are in fluid flow communication with one or more fluid inlets in the device. The hydrophilic regions comprising reagents are also in fluid flow communication with one or more test zones (e.g., the reagent region may be placed in register with the test zone to provide fluid flow communication between the reagent zone and the test zone). A device designed for assaying a single sample may comprises plural reagents disposed in the device within or in flow communication with one or more of the hydrophilic regions and in flow communication with a test zone when the hydrophilic region and test zone are in fluid flow communication.

In general, a wide variety of reagents may be disposed in the disclosed devices to detect one or more analytes in a sample. These reagents include, but are not limited to, antibodies, nucleic acids, aptamers, molecularly-imprinted polymers, chemical receptors, proteins, peptides, inorganic compounds, and organic small molecules. In a given device, one or more reagents may be adsorbed to one or more hydrophilic regions (non-covalently through non-specific interactions), or covalently (as esters, amides, imines, ethers, or through carbon-carbon, carbon-nitrogen, carbon-oxygen, or oxygen-nitrogen bonds).

Any reagent needed in the assay may be provided within, or in a separate adsorbent layer in fluid communication with a hydrophilic region. Exemplary assay reagents include protein assay reagents, immunoassay reagents (e.g., ELISA reagents), glucose assay reagents, sodium acetoacetate assay reagents, sodium nitrite assay reagents, or a combination thereof. The device described herein may comprise, without limitation, a blocking agent, enzyme substrate, specific binding reagent such as an antibody or sFv reagent, labeled binding agent, e.g., labeled antibody, may be disposed in the device within or in flow communication with one or more of the hydrophilic regions. A binder, e.g., an antibody, may be labeled with an enzyme or a colored particle to permit colorimetric assessment of analyte presence or concentration. For example, the binder may be labeled with gold colloidal particles or the like as the color forming labeling substance. Where an enzyme is involved as a label, e.g., alkaline phosphatase, horseradish peroxidase, luciferase, or β-galactosidase, an enzyme substrate may be disposed in the device within or in flow communication with one of the hydrophilic regions. Exemplary substrates for these enzymes include BCIP/NBT, 3,3',5,5'-Tetramethylbenzidine (TMB), 3,3'-Diaminobenzidine (DAB), and 2,2'-azino-bis(3-ethylbenzthiazoline-6-sulphonic acid) (ABTS), 4-methylumbelliferphosphoric acid, 3-(4-hydroxyphenyl)-propionic acid, or 4-methylumbellifer-β-D-galactoside, or the like. Preferably, the reagent(s) function to develop color in a test zone (including gradations from white to black) as an indication of the presence, absence or concentration of an analyte in a sample.

In some embodiments, a device may include many detection reagents, each of which can react with a different analyte to produce a detectable effect. Alternatively, detection reagents may be sensitive to a predetermined concentration of a single analyte.

The device also may comprise a washing reagent, or plural wash reagents such as buffers or surfactant solutions, within or in fluid communication with a hydrophilic region. Washing reagent(s) function to wash an analyte bound to a test zone by removing unbound species therein when said hydrophilic region and test zone are in fluid flow communication. For example, a suitable washing buffer may comprise PBS, detergent, surfactants, water, and salt. The composition of the washing reagent will vary in accordance with the requirements of the specific assay such as the particular capture reagent and indicator reagent employed to determine the presence of a target analyte in a test sample, as well as the nature of the analyte itself.

Alternatively, steps of a reaction using the devices disclosed herein may be washed as follows. In certain embodiments, defined hydrophilic regions in the reagent layer are left blank (i.e., the regions do not contain a reagent). Water or buffer is then added to the device via a carrier fluid inlet and the fluid passes through the device based on the three-dimensional network of channels in fluid flow communication. When the empty hydrophilic region in the reagent layer and the test zone are in fluid flow communication, the water or buffer passes through the test layer to provide a washing step for the analytes bound to the test zone. Such washing steps can be used to remove unbound analyte or other components added for the detection of the presence of an analyte. Washing steps may be repeated to achieve sufficient washing of a test zone.

Two-Dimensional Assay Devices

Figure 10:
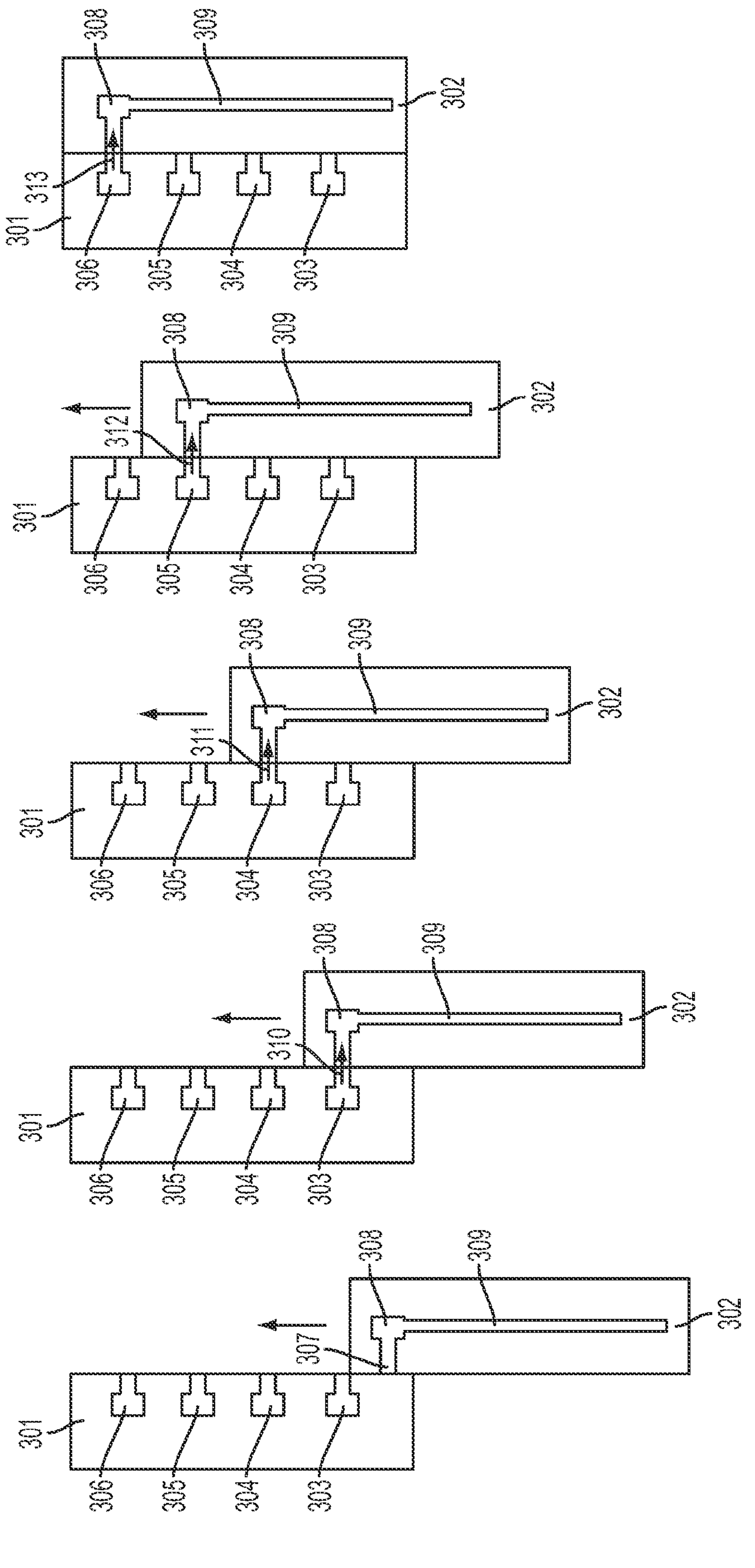
FIG. 10 illustrates an alternative, "two dimensional" embodiment of a device of the invention comprising two substantially planar layers that are parallel to one another in the same Z plane.

In another aspect, two-dimensional devices are provided for assaying fluid samples, e.g., aqueous fluid samples. Exemplary 2-D devices comprise two substantially planar members disposed parallel to one another in the same Z plane. The two layers are moveable with respect to the other, e.g., one of the two layers may slide with respect to the other in the same Z plane when placed in side-by-side contact (see FIG. 10). As shown in FIG. 10, one member 301 contains a plurality of reagents zones 303-306. The other member 302 comprises a hydrophilic region serving as a test zone 308 and a patterned channel, which provide adsorptive lateral flow within the layer. The device permits one to conduct a multi-step assay for detecting the presence, absence, or concentration of an analyte in a sample. Sample may be added directly to test zone 308, which may optionally comprise a binder for immobilizing an analyte. Alternatively, sample may be added to a hydrophilic region 303, which may be placed in fluid flow communication with region 308 via path 307. Channel 309, running the length of the member 302, has sufficient adsorptive capacity to draw (downwardly in the illustration) fluid through test zone 308 to add reagents or as a wash as the members slide and connect region 308 serially with the reagent zones in member 301. Optionally, the device may include fluid inlets, filters and the like designed to deliver fluid to the hydrophilic regions the layers.

Figure 11:
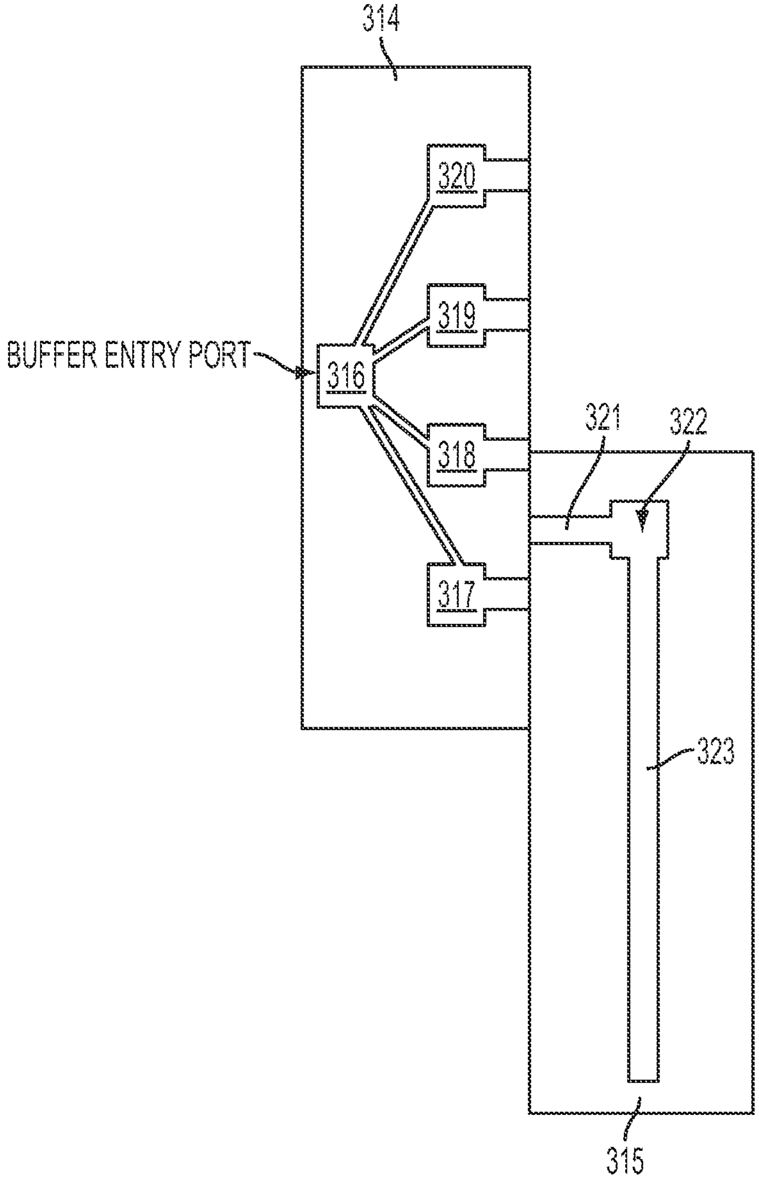
FIG. 11 illustrates how reagents may be stored and released in the device shown in FIG. 10.

In operation, in the two-dimensional device, sample is added and water is added to the reagents zones 303-306. Optionally, member 301 may be fabricated as illustrated in FIG. 11, to permit a single deposit of water to be loaded into each of the hydrophilic regions of the member simultaneously. The members then are moved relative to each other to align the channel 307 with hydrophilic region 303 of layer 301. When aligned (or when registered horizontally), the two regions are in fluid flow communication and analyte in region 308 is contacted by the reagent drawn by capillarity/adsorption from hydrophilic region 303 of layer 301 through test zone 308 and into channel 309. Similar to the description above for three-dimensional devices, multiple reagents may be and typically are deposited in the defined hydrophilic reagent zones. Accordingly, multiple steps of a reaction may be performed by sliding member 302 in the same Z plane as member 301 to expose the analyte deposition regions 308 serially to each of the reagents disposed in reagent zones 304, 305, and 306. In an exemplary embodiment, a two-dimensional device may be assembled and used to conduct one or multiple assays, e.g., an immunoassays. For example, region 308 on layer 302 may be predisposed (or spotted) with a capture antibody specific for a pre-determined analyte in a fluid sample. Sample may be added to region 303 on layer 301 (or, alternatively, sample may be added directly to region 308 on layer 302). When sample is added to region 303 on layer 301 it is transferred to the test zone 308 as region 303 is in fluid flow communication with region 308. Reagent zone 304 may be disposed (or loaded) with an antibody conjugated with a label. After a time interval, layer 302 is moved along the parallel plane to place region 308 in fluid flow communication with region 304, where, for example, labeled antibody is transferred to region 308. Reagent zone 305 may be loaded with a wash buffer for removing an unbound antibody. After a time interval, layer 302 is moved along the parallel plane to place region 308 in fluid flow communication with region 305. Wash buffer is transferred to region 308 following the addition of buffer to region 305 (or, alternatively, region 305 may be disposed with buffer salts and the buffer may be transferred to region 308 following the addition of water). Reagent zone 306 may be predisposed with a color development substrate. After a time interval, layer 302 is slid along the parallel plane to place region 308 in fluid flow communication with region 306. The color development substrate may then react with the conjugated antibody to produce a color reaction. Layer 302 may be moved out of contact with layer 301 or it may remain in contact with layer 301 for analysis of the color reaction in the test zone. The test zone 308 may be read with the naked eye or by appropriate machine (e.g., a portable scanner) or imaged with a camera phone or other device for transmission and analysis (e.g., remote analysis) of the image.

FIG. 11 provides an alternate embodiment of a two-dimensional device comprising a carrier fluid inlet (e.g., for addition of water or buffer). In this exemplary embodiment, a single carrier fluid inlet (port 316 as shown) may be placed in fluid flow communication with the plural reagent zones (e.g., reagent zones 317-320 as shown).

Analyte Detection

As described herein, the test layer or member may comprise multiple assay regions for the detection of multiple analytes. The assay regions of the device can be treated with reagents that respond to the presence of analytes in a biological fluid and that can serve as an indicator of the presence of an analyte. In some embodiments, the detection of an analyte is visible to the naked eye. For example, the hydrophilic substrate can be treated in the assay region to provide a color indicator of the presence of the analyte. Indicators may include molecules that become colored in the presence of the analyte, change color in the presence of the analyte, or emit fluorescence, phosphorescence, or luminescence in the presence of the analyte. In other embodiments, radiological, magnetic, optical, and/or electrical measurements can be used to determine the presence of proteins, antibodies, or other analytes.

In certain embodiments, analytes may be detected by direct or indirect detection methods that apply the principles of immunoassays (e.g., a sandwich or competitive immunoassay or ELISA).

In some embodiments, to detect a specific protein, an assay region of the hydrophilic substrate can be derivatized with reagents, such as antibodies, ligands, receptors, or small molecules that selectively bind to or interact with the protein. For example, to detect a specific antigen in a sample, a test zone disposed in the hydrophilic substrate may be derivatized with reagents such as antibodies that selectively bind to or interact with that antigen. Alternatively, to detect the presence of a specific antibody in the sample, a test zone disposed in the hydrophilic substrate may be derivatized with antigens that bind or interact with that antibody. For example, reagents such as small molecules and/or proteins can be covalently linked to the hydrophilic substrate using similar chemistry to that used to immobilize molecules on beads or glass slides, or using chemistry used for linking molecules to carbohydrates. In alternative embodiments, reagents may be applied and/or immobilized in a hydrophilic region by applying a solution containing the reagent and allowing the solvent to evaporate (e.g., depositing reagent into the hydrophilic region). The reagents can be immobilized by physical absorption onto the porous substrate by other non-covalent interactions.

It is understood that the interaction of certain analytes with some reagents may not result in a visible color change, unless the analyte was previously labeled. The devices disclosed herein may be additionally treated to add a stain or a labeled protein, antibody, nucleic acid, or other reagent that binds to the target analyte after it binds to the reagent in the test zone, and produces a visible color change. This can be done, for example, by providing the device with a separate area that already contains the stain, or labeled reagent, and includes a mechanism by which the stain or labeled reagent can be easily introduced to the target analyte after it binds to the reagent in the assay region. Or, for example, the device can be provided with a separate channel that can be used to flow the stain or labeled reagent from a different region of the paper into the target analyte after it binds to the reagent in the test zone. In one embodiment, this flow is initiated with a drop of water, or some other fluid. In another embodiment, the reagent and labeled reagent are applied at the same location in the device, e.g., in the test zone.

In one exemplary embodiment, ELISA may be used to detect and analyze a wide range of analytes and disease markers with the high specificity, and the result of ELISA can be quantified colorimetrically with the proper selection of enzyme and substrate. As described in greater detail below, paper-based three-dimensional ELISA (p-ELISA) devices were constructed to detect a model antigen, rabbit IgG.

Detection of an analyte in a sample may include an additional step of creating digital data indicative of an image of a developed test zone and therefore of the assay result, and transmitting the data remotely for analysis to obtain diagnostic information. Some embodiments further include equipment that can be used to image the device after deposition of the liquid in order to obtain information about the quantity of analyte(s) based on the intensity of a colorimetric response of the device. In some embodiments, the equipment is capable of establishing a communication link with off-site personnel, e.g., via cell phone communication channels, who perform the analysis based on images obtained by the equipment.

In some embodiments, the entire assay can be completed in less than 30 minutes, 20 minutes, 15 minutes, 10 minutes, or 5 minutes. The platform can have a detection limit of about 500 pM, 250 pm, 100 pM, 1 pM, 500 fM, 250 fM, or 100 fM.

Samples

The devices described herein can be used for assaying small volumes of biological samples, e.g., fluid samples. Biological samples that can be assayed using the devices described herein include, e.g., urine, whole blood, blood plasma, blood serum, sputum, cerebrospinal fluid, ascites, tears, sweat, saliva, excrement, gingival cervicular fluid, or tissue extract. In some embodiments, the volume of fluid sample to be assayed may be a drop of blood, e.g., from a finger prick, or a small sample of urine, e.g., from a newborn or a small animal. In other embodiments, the devices described herein can be used for assaying aqueous fluid samples such as industrial fluid or a water sample. The devices may also be adapted for assaying non-aqueous fluid samples for detecting, e.g., environmental contamination.

Under many aspects, a single drop of liquid, e.g., a drop of blood from a pinpricked finger, is sufficient to perform assays providing a simple yes/no answer to determine the presence of an analyte, or a semi-quantitative measurement of the amount of analyte that is present in the sample, e.g., by performing a visual or digital comparison of the intensity of the assay to a calibrated color chart. However, to obtain a quantitative measurement of an analyte in the liquid, a defined volume of fluid is typically deposited in the device. Thus, in some embodiments, a defined volume of fluid (or a volume that is sufficiently close to the defined volume to provide a reasonably accurate readout) can be obtained by patterning the paper to include a sample well that accepts a defined volume of fluid. For example, in the case of a whole blood sample, the subject's finger could be pinpricked, and then pressed against the sample well until the well was full, thus providing a satisfactory approximation of the defined volume.

Analytes

The assay reagents included in the disclosed devices are selected to provide a visible indication of the presence of one or more analytes. The source or nature of the analytes that may be detected using the disclosed devices are not intended to be limiting. Exemplary analytes include, but are not limited to, toxins, organic compounds, proteins, peptides, microorganisms, bacteria, viruses, amino acids, nucleic acids, carbohydrates, hormones, steroids, vitamins, drugs, pollutants, pesticides, and metabolites of or, antibodies to, any of the above substances. Analytes may also include any antigenic substances, haptens, antibodies, macromolecules, and combinations thereof. For example, immunoassays using the disclosed devices could be adopted for antigens having known antibodies that specifically bind the antigen.

In exemplary embodiments, the disclosed devices may be used to detect the presence or absence of one or more viral antigens, bacterial antigens, fungal antigens, or parasite antigens, cancer antigens.

Exemplary viral antigens may include those derived from, for example, the hepatitis A, B, C, or E virus, human immunodeficiency virus (HIV), herpes simplex virus, Ebola virus, varicella zoster virus (virus leading to chicken pox and shingles), avian influenza virus, SARS virus, Epstein Barr virus, rhinoviruses, and coxsackieviruses.

Exemplary bacterial antigens may include those derived from, for example, *Staphylococcus aureus, Staphylococcus epidermis, Helicobacter pylori, Streptococcus bovis, Streptococcus pyogenes, Streptococcus pneumoniae, Listeria monocytogenes, Mycobacterium tuberculosis, Mycobacterium leprae, Corynebacterium diphtheriae, Borrelia burgdorferi, Bacillus anthracis, Bacillus cereus, Clostridium botulinum, Clostridium difficile, Salmonella typhi, Vibrio chloerae, Haemophilus influenzae, Bordetella pertussis, Yersinia pestis, Neisseria gonorrhoeae, Treponema pallidum, Mycoplasm* sp., *Legionella pneumophila, Rickettsia typhi, Chlamydia trachomatis, Shigella dysenteriae*, and *Vibrio cholera.*

Exemplary fungal antigens may include those derived from, for example, *Tinea pedis, Tinea corporus, Tinea cruris, Tinea unguium, Cladosporium carionii, Coccidioides immitis, Candida* sp., *Aspergillus fumigatus*, and *Pneumocystis carinii.*

Exemplary parasite antigens include those derived from, for example, *Giardia lamblia, Leishmania* sp., *Trypanosoma* sp., *Trichomonas* sp., and *Plasmodium* sp.

Exemplary cancer antigens may include, for example, antigens expressed, for example, in colon cancer, stomach cancer, pancreatic cancer, lung cancer, ovarian cancer, prostate cancer, breast cancer, liver cancer, brain cancer, skin cancer (e.g., melanoma), leukemia, lymphoma, or myeloma.

In other embodiments, the assay reagents may react with one or more metabolic compounds. Exemplary metabolic compounds include, for example, proteins, nucleic acids, polysaccharides, lipids, fatty acids, amino acids, nucleotides, nucleosides, monosaccharides and disaccharides. For example, the assay reagent is selected to react to the presence of at least one of glucose, protein, fat, vascular endothelial growth factor, insulin-like growth factor 1, antibodies, and cytokines.

Assay Methods

Figure 9:
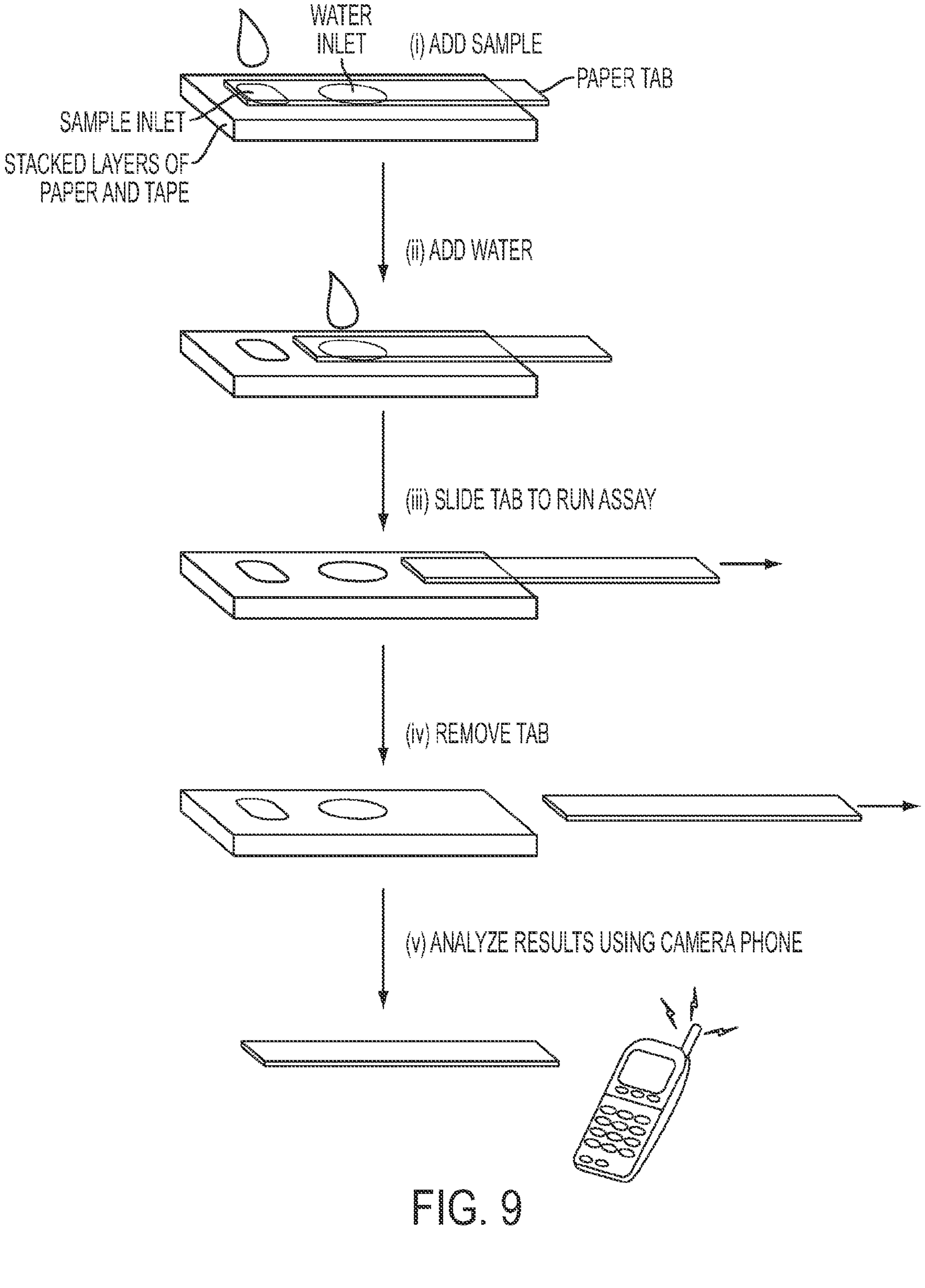
FIG. 9 is a schematic diagram illustrating a method for performing a multiplexed assay using a three-dimensional device as described herein. Distinct features of the paper-based device include sample and carrier fluid (e.g., water) inlet, patterned layers of paper and barrier film (tape) designed for storing and distributing the reagents, antigens, and antibodies, and a moveable layer for controlling fluidic flow through this device. In this exemplary embodiment, performing the assay comprises: (i) introducing the targeted sample into the sample inlet zone, (ii) introducing water into the carrier fluid inlet, (iii) sliding the moveable layer laterally through the device to facilitate washing, (iv) initiating a color reaction in the test zone by placing the test zone in fluid communication with a hydrophilic region comprising one or more detection agents (e.g., a substrate for an enzymatic reaction to produce a colored precipitate), removing the test zone from the device, and (v) capturing (and/or analyzing) the results (e.g., the color reaction) using a camera phone.

In yet another aspect, the invention provides assay methods comprising providing a device as described herein, adding a sample to the test zone, adding water or buffer to a fluid inlet, and moving one layer in relation to another to establish serial fluid flow communication between the test zone and the hydrophilic zones (illustrated in FIG. 9). This permits fluid flow between respective hydrophilic regions and the test zone for a time interval and "automatic" execution of multiple steps of the assay. Examination of the test zone permits determination of the presence, absence, or concentration of the analyte. Preferably, the assay protocol produces a color reaction, which includes the development of a grey scale from black to white, and the examination of the development of or, intensity of, the color in the test zone to determine the presence, absence, or concentration of a said analyte.

In one embodiment, an ELISA may be conducted using the disclosed device. The method may comprise the steps of: addition of a sample to the device, wherein the sample is wicked directly through the reagent layer (e.g., where the analyte is bound by labeled antibody) and into the test zone (e.g., where the analyte binds to the antigen); sliding the test layer to predefined positions noted on the test layer as stops #1, #2 and #3, where the test zones are washed with PBS; sliding the test layer to stop #4, where buffer is added to a carrier fluid inlet and substrate for the enzyme conjugated to the labeled antibody is added to the test zone based on fluid flow communication between the hydrophilic region comprising the substrate deposited therein and the test zone; and removing the strip from the device to observe the results.

Kits

In another aspect, the invention provides a kit comprising a device as described herein. The kit may optionally include one or more vials of purified water and/or buffer, e.g., PBS. The kit may additionally include a device to obtaining a blood sample (e.g., a device of making a needle stick), a device for collecting a urine sample or saliva sample or other body fluid, or a pipette for transferring water and/or buffer to the device. Further, the kit may include instructions or color charts for quantitating a color reaction.

EXAMPLES

The invention is further illustrated by the following examples. The examples are provided for illustrative purposes only, and are not to be construed as limiting the scope or content of the invention in any way.

Example 1

Portable Microfluidic Paper-Based Device for ELISA

A three-dimensional microfluidic paper-based analytical device (abbreviated "3D-μPAD") comprising movable paper test strip or layer containing one or more test zones was developed for performing ELISA. As described in greater detail below, the movable test layer may be manually moved through the device, stopping at specified points where the test zones may be placed contact with different microfluidic paths and wash reagents stored in the device. Unlike conventional ELISA, performing ELISA using the described 3D-μPAD did not require the need for pipetting or the removal of reagents and buffers. Thus, methods using the described device may be performed as a point of care assay with minimal training for the operator performing the assay.

Figure 4A:
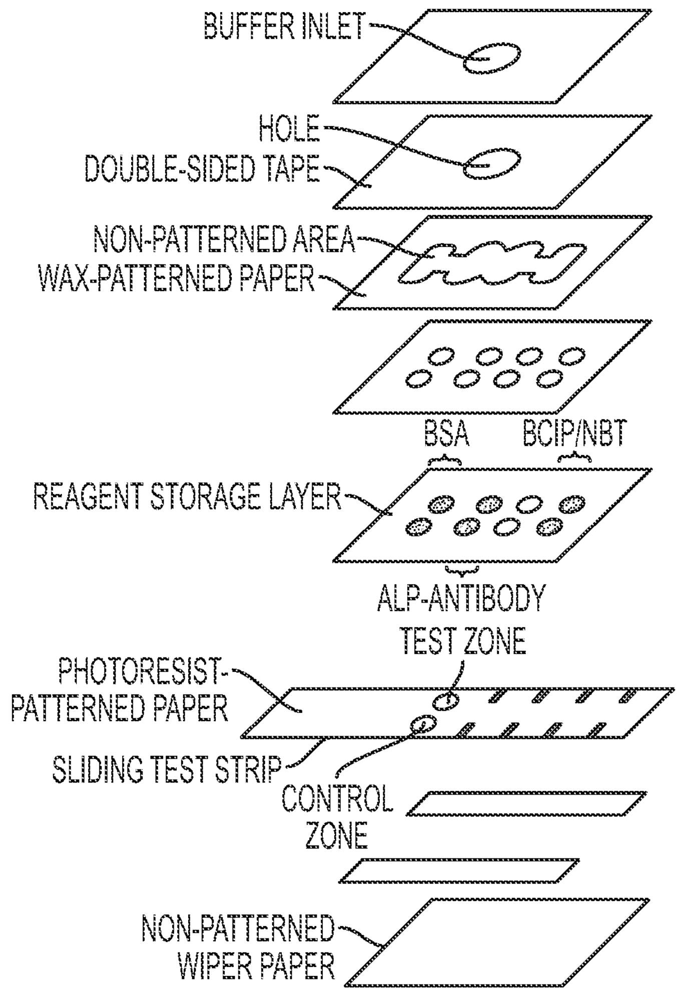
FIG. 4 (A and B) are schematic diagrams of the device described in Example 1 comprising a portable three-dimensional microfluidic paper device comprising a sliding test strip (also referred to herein as a "sliding layer," "moveable layer", "moveable test layer," or "test layer").

In the following example, a 3D-μPAD was designed to include (i) a reagent layer containing patterned zones for storing reagents used in the ELISA assay; (ii) a 3D network of channels for distributing buffer from the carrier fluid inlet to the reagent layer; (iii) a movable paper layer with test zones; and (iv) alignment marks on the movable layer to ensure that the test zones were aligned with the reagent delivery channels. Sliding the movable test layer one or more alignment marks connected the test zones with each reagent storage region in a controlled manner, such that the reagents were delivered to the test zones at specified time intervals (see FIG. 4). To minimize the wicking time of the fluid from the inlet of the device to the test zones of the movable paper layer, the length of the fluidic pathways was minimized by using a minimum number (e.g., three) of paper layers to create the 3D paper microchannels (FIG. 4A). The test zones on the sliding layer were designed to be 3 mm in diameter, so that only a small volume (2 μL) of the sample would be needed to saturate the test zone, while the colorimetric results could still be easily photographed by an inexpensive imaging device.

As depicted in FIG. 4A, portable 3D-μPADs were fabricated using chromatography paper and water-impermeable double-sided adhesive tape. Alternating layers of patterned paper and double-sided adhesive tape containing perforations for guiding fluids among layers of paper were stacked to create a paper-based 3D microfluidic device (FIGS. 4A-B) (Martinez et al. (2010) *Anal. Chem.* 82: 3-10; Martinez et al. (2008) *Proc. Natl. Acad. Sci.* 105: 19606-19611). Wax printing was used to pattern the layers of paper to form the 3D channels (layers 1, 3 and 5 from the top in FIG. 4A) (Carrilho et al. (2009) *Anal. Chem.* 81: 7091-7095). For immobilization of proteins (e.g., antibodies) within the test zones, the moveable test layer was patterned using photolithography. Without wishing to be bound by theory, residual photoresist present on the paper fibers, after patterning, made the test zones more hydrophobic (layer 6 from the top of FIG. 4A) (Martinez et al. (2007) *Angew. Chem. Int. Ed.* 46: 1318-1320).

Fabrication and Assembly of the Portable 3D-μPAD

For the experiments described in Examples 1-3, the 3D-μPAD (FIG. 4A) comprised i) three layers of wax-patterned 1 Chr chromatography paper (Whatman), which formed the 3D microfluidic channels, ii) one layer of photolithography-patterned 3 mm Chr chromatography paper (Whatman) as the movable test layer, iii) one layer of non-patterned wiper paper (VWR Spec-Wipe® 3 wiper) as the bottom substrate, and iv) three layers of laser-cut double-sided tape (3M carpet tape) for device assembly.

The 1Chr chromatography paper was patterned via wax printing (Carrilho et al. (2009) supra). A sheet of 1Chr chromatography paper was printed with a wax printer (Xerox phaser 8560), and baked in a 150° C. oven for two minutes. The baking step allowed the printed wax to melt and diffuse into the paper to form hydrophobic barriers for the paper channels.

The 3 mm Chr chromatography paper was patterned using photolithography. A sheet of paper was impregnated with SU8 2010 photoresist (MicroChem) and pre-baked on a 110° C. hotplate for 20 minutes to remove the solvent from the photoresist. The paper was then cooled to room temperature and exposed under a UV light source (Uvitron IntelliRay 600) for 41 seconds through a transparency mask. The paper was then post-baked for two minutes at 110° C., and the patterns were developed in an acetone bath for five minutes, followed by a single rinse in acetone and a single rinse in 70% isopropyl alcohol. Finally, the paper was blotted between two paper towels, rinsed again with 70% isopropyl alcohol, blotted again, and allowed to dry under ambient conditions for at least 1 hour.

The double side tape was cut using a laser cutter (Versalaser VLS 3.50).

The 3D-μPAD was assembled by manually stacking layers of patterned paper and double-sided adhesive tape. The entire assembly process took approximately two minutes (excluding the time to pattern the paper and tape). Since transferring the reagents from the storage layer to the test zones using PBS buffer lowered the concentrations of the reagents, high concentrations of reagents and antibody were incorporated into the reagent storage layer during the assembly of the device (FIG. 4A). The following quantities of reagents were spotted in the reagent storage layer using a pipette: i) 1 μL of a blocking buffer (0.25% (v/v) Tween-20 and 5% (w/v) bovine serum albumin (BSA) in PBS buffer), ii) 1 μL at solution of Alkaline Phosphatase (ALP)-conjugated detection antibody (20 μg/mL), and iii) 1 μL solution of a BCIP/NBT substrate (13.4 mM BCIP, 9 mM NBT, 25 mM $MgCl_2$, 500 mM NaCl, and 0.25% Tween in 500 mM Tris buffer).

Protocol for Carrying Out ELISA on a 3D-μPAD

Figure 5:
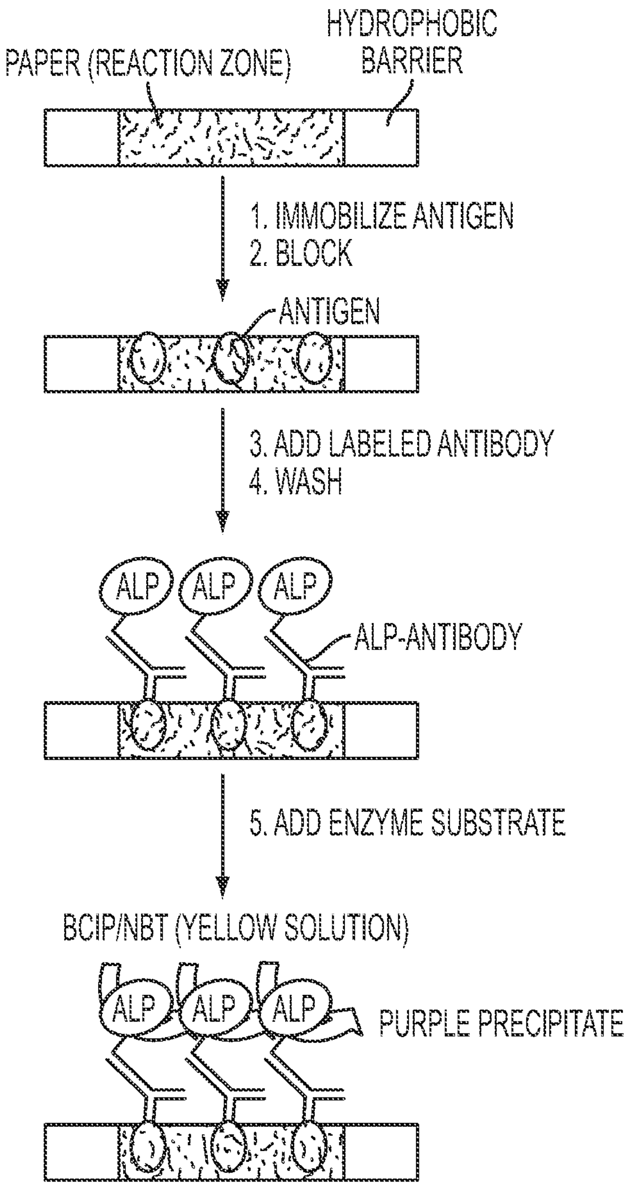
FIG. 5 (1-5) is a diagram showing the steps of a reaction for detection of rabbit IgG as a sample antigen conducted using a device described herein, focusing on the reactions and steps occurring in the test zone.

An ELISA on a 3D-μPAD was performed by (i) immobilizing antigens in the test zone; (ii) blocking the surface of the cellulose fibers of the paper to inhibit non-specific absorptions of proteins; (iii) labeling immobilized antigens with enzyme-conjugated detection antibodies; (iv) washing away un-bound detection antibodies; and (v) spotting enzyme substrates to produce colorimetric output signals (FIG. 5). Each step of the ELISA was predetermined and the reagents for each step were included in defined hydrophilic regions during the fabrication of the device. Thus, a user of the device would only need to add the sample and washing buffer and manipulate the sliding test layer.

A colorimetric readout was selected for carrying out ELISA on a 3D-μPAD because it permitted the use of a camera phone or a portable scanner for quantifying results, and could be easily integrated with cell-phone-based systems for telemedicine (Martinez et al. (2008) *Anal. Chem.* 80: 3699-3707). Further, colorimetry provides a simple and practical option for use in resource-limited settings. To carry out the colorimetric assay, an enzyme/substrate pair was chosen that would produce a dark color to ensure good contrast with the white background of the paper. ALP (alkaline phosphate) and BCIP/NBT (5-bromo-4-chloro-3-indolyl phosphate and nitro blue tetrazolium) were used because they produced a color change from clear (or white on paper) to dark purple. A wide variety of ALP-conjugated antibodies are commercially available (McGadey (1970) *Histochemie* 23: 180-184; Leary et al. (1983) *Proc. Natl. Acad. Sci.* 80: 4045-4049). Furthermore, the ALP system is well-characterized, and works reliably in a number of different applications (Cheng et al. (2010) *Angew. Chem. Int. Ed.* 49: 4771-4774; Blake et al. (1984) *Anal. Biochem.* 136: 175-179).

Figure 6:
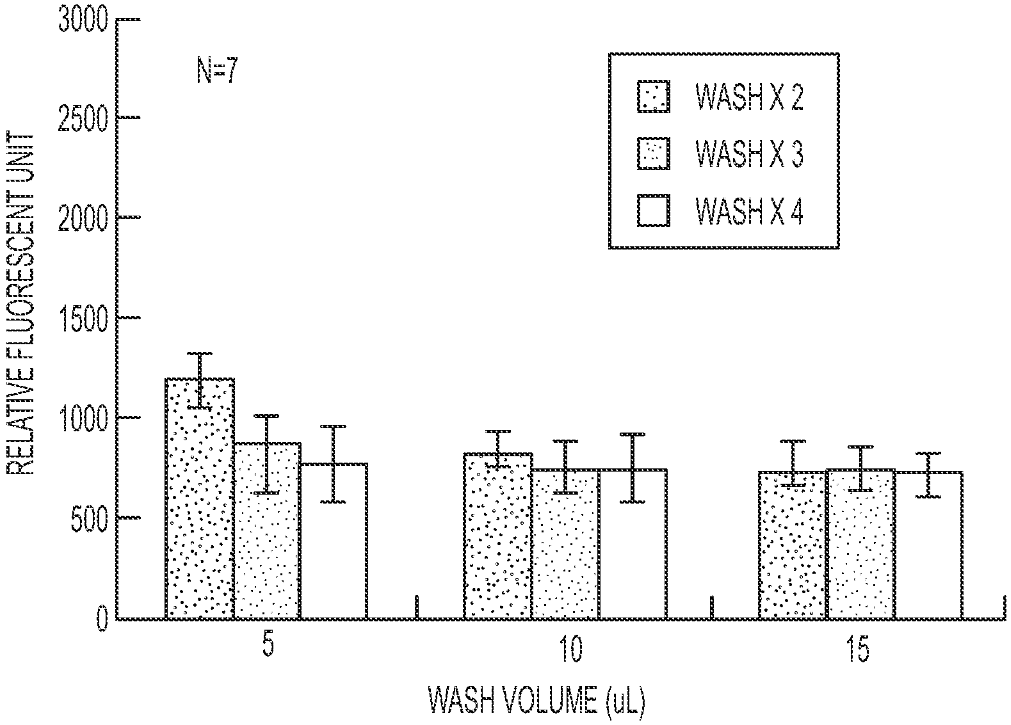
FIG. 6 is a graph showing a comparison of fluorescent intensity, which corresponds to the amount of residual unbound protein (Cy5-IgG), from test zones (N=7) that were blocked, incubated with 20 μg/mL Cy5-IgG for one minute, and finally washed with three different protocols, as identified thereon. The error bars represent one standard deviation (s.d.).

To optimize the washing steps for removing unbound proteins from the test zones, nine different protocols were assessed. A solution of IgG (20 μg/mL) labeled with fluorescent Cy5 dye was incubated on blocked test zones for 1 minute. The sliding test layer was inserted into the device, and the test zones (n=7) were washed with different combinations of buffer volumes and washing times. The fluorescent signal of the test zone, which corresponded to the amount of residual unbound protein, was quantified using a fluorescent scanner (FIG. 6; the error bars represent one standard deviation). It was determined that washing the test zones with 10 μL of PBS buffer three times provided effective removal of the unbound protein, while using the minimum number of washing steps. (IgG labeled with Cy5 (011-170-003) was purchased from Jackson ImmunoResearch.)

Figure 4B:
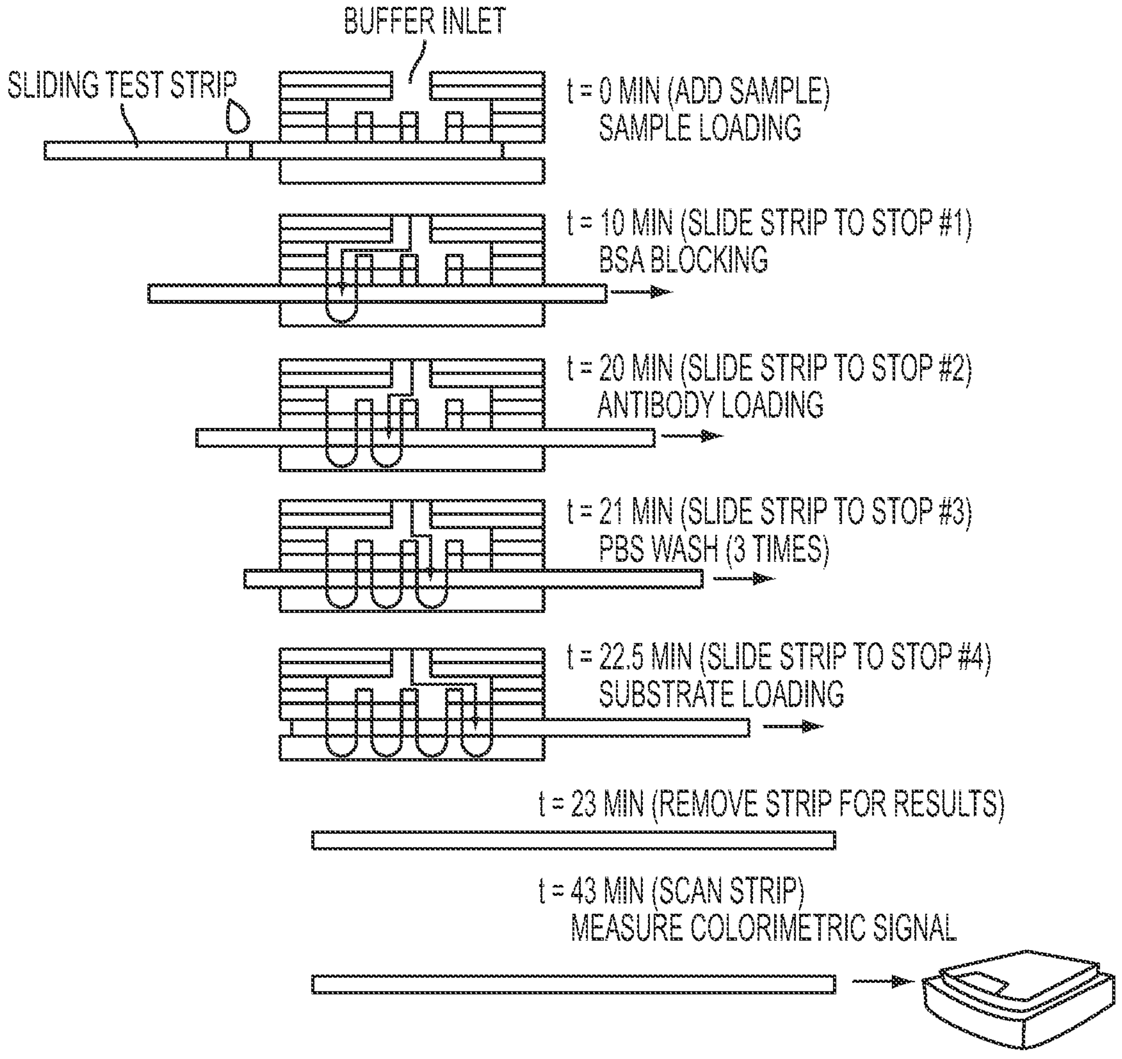

FIG. 4B illustrates the operating steps for running an ELISA using a 3D-μPAD. Using an assembled device, 2 μL of a solution containing the desired antigen was spotted onto the test zones of a paper to allow antigens to adsorb onto the surface of the cellulose fibers of the paper (FIG. 4C). The paper was allowed to dry for 10 minutes under ambient conditions. Next, the test zone on the test layer was slid to the first reagent storage zone (by aligning the "stop #1" mark as seen in FIG. 4C with the right-side edge of the device), and a 25 μL drop of PBS buffer was added to the inlet of the device to transfer the blocking buffer to the test zones for blocking non-specific absorptions of proteins. This was followed by a 10 minute incubation period. It was determined that in the first drop of the 25 μL of PBS buffer, approximately 15 μL was consumed in wetting the microfluidic channels and the rest (~10 μL) was used to transfer the blocking buffer. Next, the test layer was slid to the "stop #2" mark, and a 10 μL drop of PBS buffer was added for transferring the Alkaline Phosphatase (ALP)-conjugated antibody from the reagent storage layer to the test zones. This step was followed by a one minute incubation period. Subsequently, the test strip was slid to the "stop #3" mark, and the test zone was washed three times by adding 10 μL drops of PBS buffer to the buffer inlet. Finally, a 10 μL drop of PBS buffer was added in order to transfer the ALP substrate from the reagent storage layer to the test zones. The test layer was extracted from the device, and the enzymatic reaction was allowed to proceed for 20 minutes under ambient conditions. The test layer was scanned using a photo scanner (Perfection 1640, EPSON, set to "color photo scanning", 600 dpi resolution), and the intensity of the color was quantified using the ImageJ software (public software provided by the National Institutes of Health; available at http://rsbweb.nih.gov/ij/).

Example 2

Figure 7A:
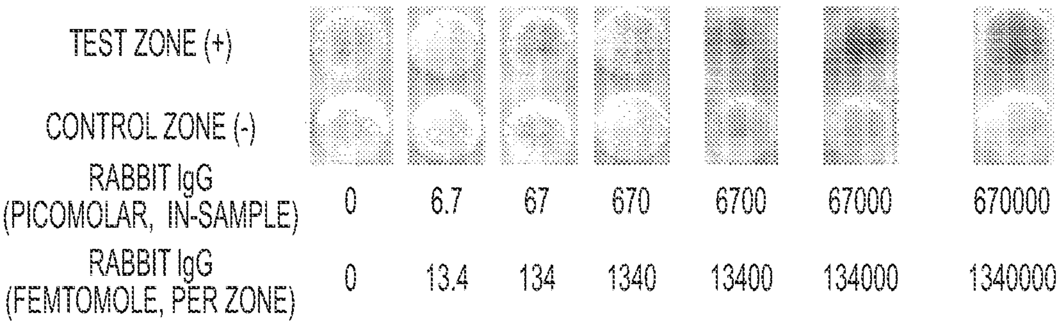
FIG. 7 (A and B) show experimental results for detection of rabbit IgG using a device embodying the invention described herein.

Assessing Rabbit IgG Using a Portable Microfluidic Paper-Based Device for ELISA In this example, rabbit IgG was used as a model analyte to assess the performance of the portable microfluidic paper-based device for ELISA. Rabbit IgG in ten-fold dilutions (6.7 picomolar to 670 nanomolar) was added to the test zone of the device. PBS buffer was used as a control in the control zone. The mean intensity of the purple color from both the test (top) and control (bottom) zones was measured (FIG. 7A). The final ELISA output signal was determined from the difference between the measured mean intensity values of the test and control zones. This difference was proportional to the amount of rabbit IgG spotted on paper.

Figure 7B:
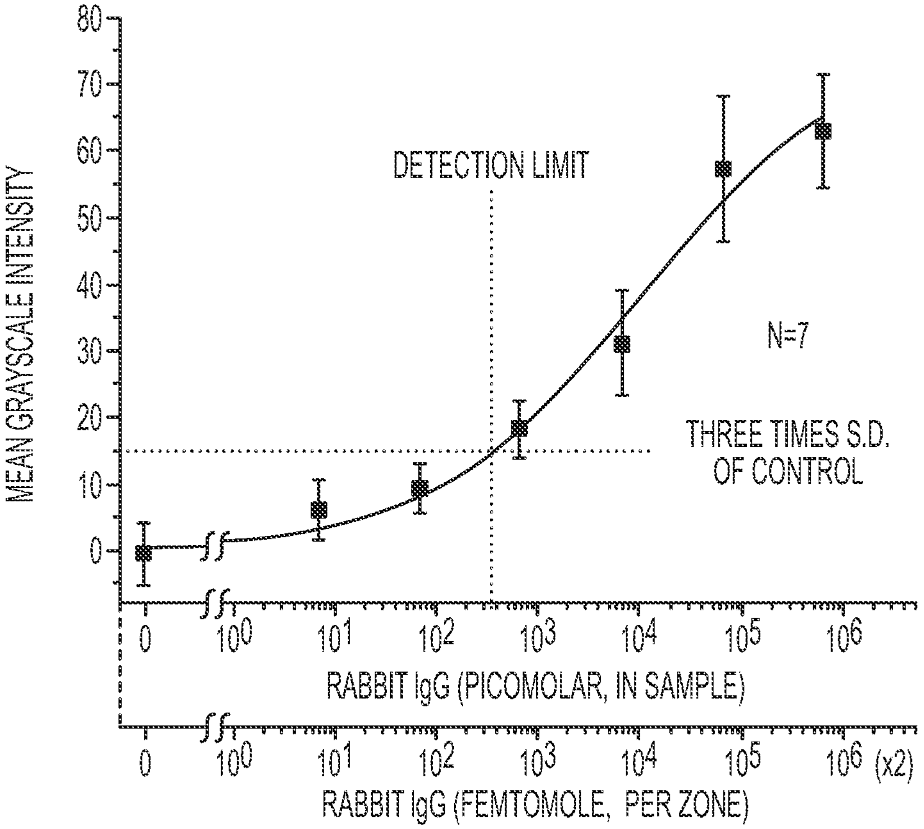

As depicted in FIG. 7B, the calibration data was presented as the output colorimetric signal versus the concentration of rabbit IgG in the sample and the amount of rabbit IgG spotted on the test zone (n=7). The experimental data from the series of rabbit IgG dilutions was fitted into a sigmoidal curve using the Hill Equation and nonlinear regression. The solid line represents a non-linear regression of Hill Equation: $I=I_{max}[L]^n/[L]^n+[L_{50}]^n$), where $I_{max}=75.5\pm10.1$, $[L_{50}]=9.5\pm8.2$ nanomolar, or $[L_{50}]=19.1\pm16.3$ nanomole/zone, $n=0.43\pm0.09$, and $R^2=0.98$. The error bars represent one standard deviation (s.d.). The linear portion of the sigmoidal curve ranges approximately within the concentrations of $10^2$-$10^5$ picomolar, or the amounts of $10^2$-$10^5$ femtomole/zone.

The detection limit of ELISA for rabbit IgG on the 3D-μPAD was 330 picomolar or 655 femtomole/zone, as defined by the concentration of rabbit IgG in a sample, or the amount of rabbit IgG spotted on the test zone that generated a colorimetric signal which was three times the standard deviation (s.d.) of the signals from the control.

Rabbit IgG (I5006), rabbit anti-IgG (A3687), BCIP/NBT, and rabbit serum were purchased from Sigma-Aldrich (St. Louis, Mo.). Commercial mouse IgG ELISA kit (Catalog Number: 11333151001) was purchased from Roche Applied Science (Indianapolis, Ind.).

Example 3

Figure 8A:
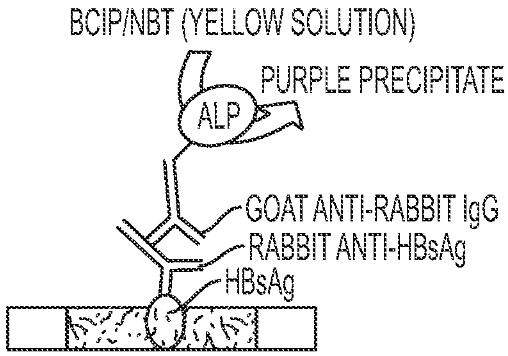
FIG. 8 (A) is a schematic diagram of an ELISA format for detection of HBsAg in rabbit serum using a three-dimensional device as described herein; (B) is an illustration of the locations of stored reagents disposed in hydrophilic regions that may be placed in fluid flow communication with the test zones (e.g., sample test zone and control zone) of a moveable layer for the detection of HBsAg; and (C) shows experimental results for detection of HBsAg in the serum samples using the described device.
Figure 8B:
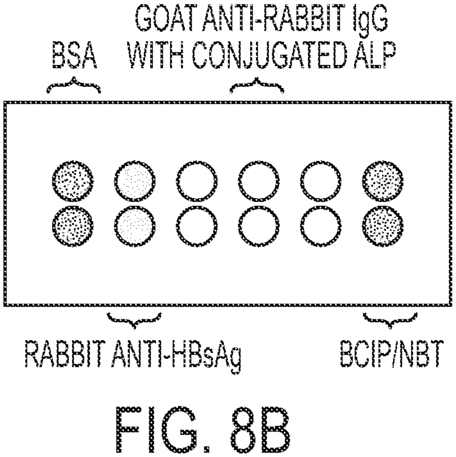

Assessing the Hepatitis B Surface Antigen (HBsAg) Using a Portable Microfluidic Paper-Based Device for ELISA In this example, the 3D-μPADs described herein were used to detect hepatitis B surface antigen (HBsAg) in rabbit serum (FIG. 8). The assay protocol was different from the ELISA protocol described previously for the detection of IgG (as shown in FIG. 5). A primary antibody (e.g., rabbit-anti HBsAg) and an ALP-conjugated secondary antibody (e.g., goat anti-rabbit IgG conjugated with ALP) were used together to label HBsAg (FIG. 8A). The design of the device allowed for flexible adjustment of the number of storage zones on the reagent storage layer. As shown in FIG. 8B, additional reagents were stored in the reagent layer of this device than those in the portable ELISA for rabbit IgG described in Example 2 (e.g., from left to right, BSA; rabbit anti-HBsAg; no reagent in this zone—for washing with PBS; goat anti-rabbit IgG with conjugated ALP; no reagent in this zone—for washing with PBS; and BCIP/NBT). The additional reagents permitted different types of biochemical analyses to be performed on the 3D-μPADs.

For detecting HBsAg in serum, the following quantities of reagents in the reagent storage layer were used during device assembly (FIG. 8B): i) 1 μL of a blocking buffer (0.25% (v/v) Tween-20 and 5% (w/v) bovine serum albumin (BSA) in PBS), ii) 1 μL of a solution of rabbit HBsAg antibody (20 μg/mL), iii) 1 μL of a solution of ALP-conjugated goat anti-rabbit IgG (20 μg/mL); and iv) 1 μL of a solution of BCIP/NBT substrate (13.4 mM BCIP, 9 mM NBT, 25 mM $MgCl_2$, 500 mM NaCl, 0.25% Tween in 500 mM Tris buffer).

Purified HBsAg (42 nM) was diluted by 1:10 and 1:100 in rabbit serum. Rabbit serum without HBsAg was used as the control. Operation of the device was similar to that described above for detection of rabbit IgG. Briefly, 2 μL of a solution of the serum sample was spotted to the test zones, followed by a 10-minute incubation under ambient conditions. Next, the test strip was slid to align the test zones with the first column of storage zones (FIG. 9B), and a 35-μL (25 μL for wetting the paper channels, and 10 μL for transferring the reagent) drop of PBS was added to the inlet of the device to transfer the blocking buffer to the test zones and block the test zones. Subsequently, the test zones were successively slid to different columns of storage zones, and 10-μL drops of PBS were added to either wash or transfer reagents to the test zones to complete the ELISA. The results were finally scanned and analyzed using the ImageJ software.

Figure 8C:
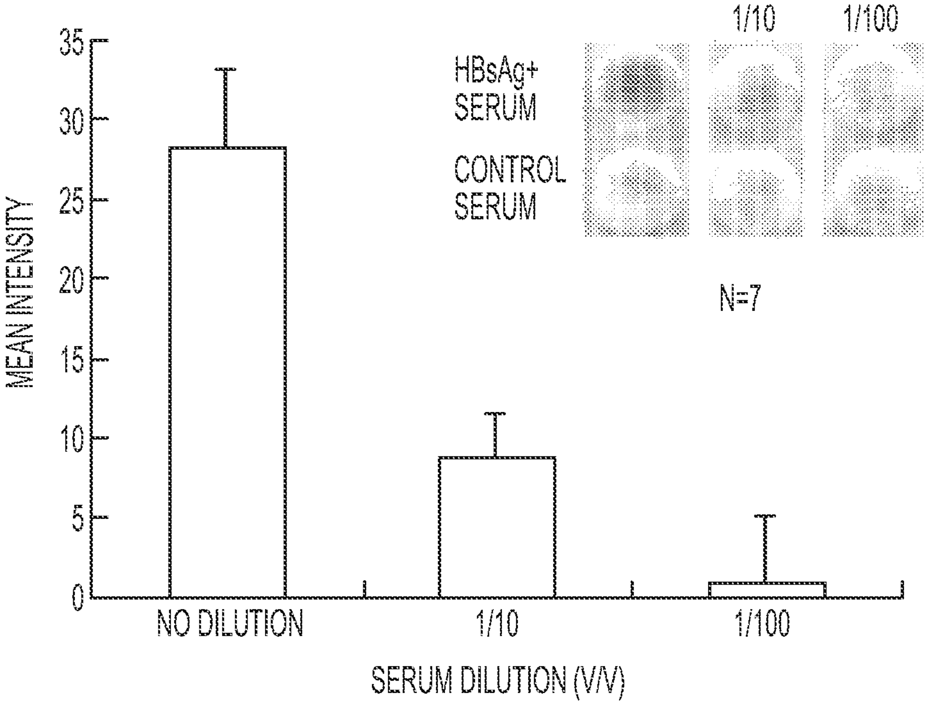

The yellowish color of the serum samples did not significantly impair the accuracy of detection, since the signal from the control zone effectively canceled the error induced by the color of the serum. As shown in FIG. 8C, the inset images show the colorimetric signals from HBsAg-positive and control serum samples. HBsAg-positive signal was detectable in the serum samples after a 1:10 dilution. This result suggested a potential for the use of the portable ELISA in detecting infectious diseases. (Error bars in 8C represent one standard deviation.)

Hepatitis B surface antigen (PIP002) was purchased from ABD Serotec (Raleigh, N.C.), and rabbit anti-HBsAg (PA1-86201) and goat anti-rabbit IgG (31340) were purchased from Pierce Biotechnology (Rockford, Ill.).

The portable ELISA using a 3D-μPAD described herein has several surprising advantages over conventional ELISA in plastic well plates, including it is more rapid, it consumes smaller volumes (2 μL) of sample and reagents, does not require advanced equipment or multiple reagents to run the assay. Further, the portability, low cost, low sample volumes and reagents, and minimal manipulation of fluids combined with the advantage of ELISA to detect different disease markers and producing a colorimetric readout for cell-phone-based telemedicine, the 3D-μPAD described herein can be used in resource-limited or remote settings.

INCORPORATION BY REFERENCE

The entire disclosure of each of the patent documents and scientific articles cited herein is incorporated by reference for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

We claim:

1. A device for assay of a fluid sample, the device comprising:

at least first and second substantially planar members disposed in the same or parallel planes, wherein the first substantially planar member is a porous, hydrophilic, adsorbent material comprising fluid-impermeable barriers that define boundaries of plural hydrophilic regions and the second substantially planar member defines a test zone for presentation of a sample for assay;

said plural hydrophilic regions and said test zone comprising porous, hydrophilic, adsorbent material for transfer of fluid within the porous, hydrophilic, adsorbent material by capillary action;

said fluid-impermeable barriers penetrating the first planar member to define the boundaries of the plural hydrophilic regions through which fluid flows by capillary action;

said members being moveable relative to each other to permit establishment of fluid flow communication serially between at least two of said hydrophilic regions and the test zone;

a reagent disposed in said device within or in flow communication with one of said hydrophilic regions and in flow communication with said test zone when said one hydrophilic region and test zone are in fluid flow communication.

2. The device of claim 1 comprising at least two separate test zones.

3. The device of claim 2 further comprising at least two reagents disposed in said device within or in flow communication with separate said hydrophilic regions and in flow communication with respective said separate test zones when said respective hydrophilic regions and test zones are in fluid flow communication, thereby to permit execution of assays for multiple analytes substantially simultaneously.

4. The device of claim 1 further comprising a positive or a negative control zone in the member comprising the test zone.

5. The device of claim 1 further comprising in the member comprising the test zone a plurality of positive control zones comprising known concentrations of an analyte thereby to permit assessment of concentration of an analyte in a sample.

6. The device of claim 1 comprising plural reagents for treating said sample in said device within or in flow communication with one or more of said hydrophilic regions and in flow communication with said test zone when said one hydrophilic region and test zone are in fluid flow communication.

7. The device of claim 1 wherein a said reagent functions to develop color in a said test zone as an indication of the presence, absence or concentration of an analyte in a sample.

8. The device of claim 1 comprising a washing reagent within or in fluid communication with a second hydrophilic zone which washing reagent functions to wash an analyte bound to a test zone by removing unbound species therein when said second hydrophilic region and test zone are in fluid flow communication.

9. The device of claim 1 wherein establishment of fluid flow communication between a said hydrophilic region and the test zone is effected by movement of said first and second members relative to each other to register vertically or horizontally a said test zone and a said hydrophilic region.

10. The device of claim 1 further comprising a carrier fluid inlet and a series of flow paths between said carrier fluid inlet and said hydrophilic regions.

11. The device of claim 1 further comprising a sample inlet in fluid communication with a said test zone.

12. The device of claim 1 further comprising a sample filter upstream of and in fluid communication with a said test zone.

13. The device of claim 1 further comprising a reagent reservoir upstream of and in fluid communication with a said test zone comprising a reagent for pre-treating a sample.

14. The device of claim 1 wherein said test zone comprises an immobilized analyte binder.

15. The device of claim 1 comprising a blocking agent disposed in said device within or in flow communication with one of said hydrophilic regions.

16. The device of claim 1 comprising an antibody reagent disposed in said device within or in flow communication with one of said hydrophilic regions.

17. The device of claim 14 comprising a labeled antibody reagent.

18. The device of claim 17 wherein the antibody is labeled with an enzyme, a fluorophore, or a colored particle to permit colorimetric assessment of analyte presence or concentration.

19. The device of claim 1 comprising an enzyme substrate disposed in said device within or in flow communication with one of said hydrophilic regions.

20. The device of claim 18 wherein the enzyme is alkaline phosphatase or horseradish peroxidase.

21. The device of claim 19 wherein the substrate is selected from the group consisting of BCIP/NBT, 3,3',5,5'-Tetramethylbenzidine (TMB), 3,3'-Diaminobenzidine (DAB) and 2,2'-azino-bis(3-ethylbenzthiazoline-6-sulphonic acid) (ABTS).

22. The device of claim 1 wherein the analyte is selected from the group consisting of: viral antigens, bacterial antigens, fungal antigens, parasitic antigens, cancer antigens, and metabolic markers.

23. The device of claim 1 further comprising visual indicia of the establishment of fluid communication of a test zone with plural said hydrophilic regions.

24. The device of claim 1 wherein said members comprise a material selected from the group consisting of paper, cloth, and polymer film.

25. The device of claim 1 wherein said fluid-impermeable barriers that define boundaries of said plural hydrophilic regions are produced by screening, stamping, printing or photolithography and comprise a photoresist, wax, poly(methylmethacrylate), an acrylate polymer, polystyrene, polyethylene, polyvinylchloride, a fluoropolymer, or a photo-polymerizable polymer that forms a hydrophobic polymer.

26. The device of claim 1 further comprising a fluid-impermeable layer disposed between adjacent layers and defining openings permitting fluid flow therethrough.

27. The device of claim 1 further comprising an adsorbent layer for drawing fluid from or through a said hydrophilic region and through a said test zone.

28. An assay method comprising providing the device of claim 1, adding a sample to said test zone, moving one said layer in relation to another to establish serially fluid communication between a test zone and said hydrophilic zones to permit fluid flow therebetween for a time interval and to execute multiple steps of an assay, and examining said test zone to determine the presence, absence, or concentration of an analyte.

29. An assay method comprising providing the device of claim 1, adding a sample to said test zone, moving one said layer in relation to another to establish serially fluid communication between a test zone and said hydrophilic zones to permit fluid flow therebetween for a time interval and to execute multiple steps of an assay, and examining the development of or intensity of color development in said test zone to determine the presence, absence, or concentration of an analyte.

30. The method of claim 29 comprising the additional step of creating digital data indicative of an image of said test zone and therefore of the assay result, and transmitting the data remotely for analysis to obtain diagnostic information.

31. The device of claim 1 wherein said members comprise paper.

32. The device of claim 26 wherein said members comprise paper.

33. The device of claim 31 wherein said fluid-impermeable barriers that define boundaries of said plural hydrophilic regions comprise wax.

34. The device of claim 32 wherein said fluid-impermeable barriers that define boundaries of said plural hydrophilic regions comprise wax.

* * * * *